US012714738B2

(12) United States Patent
Ziegelaar et al.

(10) Patent No.: US 12,714,738 B2
(45) Date of Patent: Aug. 25, 2026

(54) METHODS AND AGENTS FOR TREATING ACUTE NEUROINFLAMMATORY INJURY

(71) Applicant: Implicit Bioscience Limited, Woolloongabba (AU)

(72) Inventors: Brian W. Ziegelaar, Wakerley (AU); David T. Crowe, Sammamish, WA (US); Garry Llewellyn Redlich, East Brisbane (AU)

(73) Assignee: Implicit Bioscience Limited, Woolloongabba (AU)

(*) Notice: Subject to any disclaimer, the term of this patent is extended or adjusted under 35 U.S.C. 154(b) by 1218 days.

(21) Appl. No.: 17/629,763

(22) PCT Filed: Jul. 24, 2020

(86) PCT No.: PCT/US2020/043619
§ 371 (c)(1),
(2) Date: Jan. 24, 2022

(87) PCT Pub. No.: WO2021/016601
PCT Pub. Date: Jan. 28, 2021

(65) Prior Publication Data
US 2022/0249610 A1 Aug. 11, 2022

(30) Foreign Application Priority Data
Jul. 25, 2019 (AU) ................................ 2019902642

(51) Int. Cl.
*A61K 39/395* (2006.01)
*A61K 38/17* (2006.01)
*A61P 25/00* (2006.01)
*A61P 29/00* (2006.01)
*C07K 16/28* (2006.01)

(52) U.S. Cl.
CPC .......... *A61K 38/1774* (2013.01); *A61P 25/00* (2018.01); *A61P 29/00* (2018.01); *C07K 16/2896* (2013.01); *A61K 2121/00* (2013.01)

(58) Field of Classification Search
None
See application file for complete search history.

(56) References Cited

U.S. PATENT DOCUMENTS 5,820,858 A 10/1998 Leturcq et al.
6,444,206 B1 9/2002 Leturcq et al.
7,326,569 B2 2/2008 Leturcq et al.
2006/0121574 A1 6/2006 Allison
2010/0233159 A1* 9/2010 Relton ................ A61K 38/193 424/130.1

FOREIGN PATENT DOCUMENTS

WO WO-2002042333 A1 5/2002
WO WO-2006/129849 12/2006
WO WO-2008/088902 7/2008
WO WO-2018/165720 9/2018
WO WO-2018191786 A1 10/2018

OTHER PUBLICATIONS

Beschorner et al., "CD14 expression by activated parenchymal microglia/macrophages and infiltrating monocytes following human traumatic brain injury," Acta Neuropathologica (2002) 103:541-549.
Wang et al., "The inflammatory response in stroke," Journal of Neuroimmunology (2007) 184:53-68.
NIH National Library of Medicine, PubChem SID 160709229, "Substance record Atibuclimab" Jan. 8, 2024; 1-4.
Abeysinghe et al., (2015). "Pre-differentiation of human neural stem cells into GABAergic neurons prior to transplant results in greater repopulation of the damaged brain and accelerates functional recovery after transient ischemic stroke," Stem Cell Res. Ther., 6:186, 19 pages.
Adachi et al., (1999). "Inhibition by a CD14 monoclonal antibody of lipopolysaccharide binding to murine macrophages," J. Endotoxin Res., 5:139-146.
Axtelle et al., (2001). "IC14, a CD14 specific monoclonal antibody, is a potential treatment for patients with severe sepsis," J. Endotoxin Res., 7:310-314.
Balkaya et al., (2018). "Behavioral outcome measures to improve experimental stroke research," Behav. Brain Res., 352:161-171, 36 pages.
Bazil et al., (1986). "Biochemical characterization of a soluble form of the 53-kDa monocyte surface antigen," Eur. J. Immunol., 16(12):1583-1589.
Bird et al., (1988). "Single-chain antigen-binding proteins," Science, 242:423-426.
Carter et al., (1992). "Humanization of an anti-p185HER2 antibody for human cancer therapy," Proc. Natl. Acad. Sci. USA, 89:4285-4289.
Chothia (1992). "Structural repertoire of the human VH segments," J. Mol. Biol., 227:799-817.
Chothia et al., (1987). "Canonical structures for the hypervariable regions of immunoglobulins," J. Mol. Biol., 196:901-917.
Chothia et al., (1989). "Conformations of immunoglobulin hypervariable regions," Nature, 342:877-883.
Clark et al., (1997). "Monofilament intraluminal middle cerebral artery occlusion in the mouse," Neurol. Res., 19:641-8.
DiSabato et al., (2016). "Neuroinflammation: the devil is in the details," Journal of Neurochemistry, 139(Supp. 2):136-153.
Foote et al., (1992). "Antibody framework residues affecting the conformation of the hypervariable loops," J. Mol. Biol., 224:487-499.

(Continued)

*Primary Examiner* — Michael D Pak
(74) *Attorney, Agent, or Firm* — Morrison & Foerster LLP

(57) ABSTRACT

This disclosure relates generally to methods and agents for treating acute neuroinflammatory injury, such as stroke (e.g. ischemic stroke or hemorrhagic stroke), hypoxic-ischemic brain injury, traumatic brain injury, subarachnoid hemorrhage and intracerebral hemorrhage. In particular, the present disclosure relates to the use of CD14 antagonist antibodies for treating acute neuroinflammatory injury.

16 Claims, 6 Drawing Sheets

Specification includes a Sequence Listing.

(56) References Cited

OTHER PUBLICATIONS

Huston et al., (1988). "Protein engineering of antibody binding sites: recovery of specific activity in an anti-digoxin single-chain Fv analogue produced in *Escherichia coli*," Proc. Natl. Acad. Sci., 85:5879-5883.
Janova et al., (2016). "CD14 is a key organizer of microglial responses to CNS infection and injury," Glia, 64:635-649.
Jones et al., (1986). "Replacing the complementarity-determining regions in a human antibody with those from a mouse," Nature, 321:522-525.
Juan et al., (1995). "Identification of a lipopolysaccharide binding domain in CD14 between amino acids 57 and 64," J. Biol. Chem., 270(10):5219-5224.
Juan et al., (1995). "Identification of a Domain in Soluble CD14 Essential for Lipopolysaccharide (LPS) Signaling but Not LPS Binding," J. Biol. Chem., 270(29):17237-17242.
Leturcq et al., (1996). "Antibodies against CD14 protect primates from endotoxin-induced shock," J. Clin. Invest., 98:1533-1538.
MacCallum et al., (1996). "Antibody-antigen interactions: contact analysis and binding site topography," J. Mol. Biol., 262(5):732-745.
McCann et al., (2014). "Nox2 knockout delays infarct progression and increases vascular recovery through angiogenesis in mice following ischaemic stroke with reperfusion," PLoS One, 9:e110602, 13 pages.
Padlan et al., (1995). "Identification of specificity-determining residues in antibodies," FASEB J., 9:133-139.
Presta, (1992). "Antibody engineering," Curr. Op. Struct. Biol., 2:593-596.
Riechmann et al., (1988). "Reshaping human antibodies for therapy," Nature, 332:323-327.
Sandhu, (1992). "Protein Engineering of Antibodies," Crit. Rev. Biotech., 12:437-462.
Singer et al., (1993). "Optimal humanization of 1B4, an anti-CD18 murine monoclonal antibody, is achieved by correct choice of human V-region framework sequences," J. Immunol., 150:2844-2857.
Stinear, (2017). "Prediction of motor recovery after stroke: advances in biomarkers," Lancet Neurol., 16:826-836.
Tasaka et al., (2003). "Effect of CD14 Blockade on Endotoxin-Induced Acute Lung Injury in Mice," Am. J. Respir. Cell. Mol. Biol., 29(2):252-258.
Tato et al., (2008). "SnapShot: Cytokines III," Cell, 132(5):900, 900.e1, 2 pages.
Tato et al., (2008). "SnapShot: Cytokines II," Cell, 132:500, 500.e1, 2 pages.
Tato et al., (2008). "SnapShot: Cytokines I," Cell, 132(2):324, 324.e1, 2 pages.
Tempest et al., (1991). "Reshaping a Human Monoclonal Antibody to Inhibit Human Respiratory Syncytial Virus Infection in Vivo," Biotechnology, 9:266-271.
Van Voohris et al., (1983). "Specific antimononuclear phagocyte monoclonal antibodies. Application to the purification of dendritic cells and the tissue localization of macrophages," J. Exp. Med., 158:126-145.
Verhoeyen et al., (1988). "Reshaping human antibodies: grafting an antilysozyme activity," Science, 239:1534-1536.
Ward et al., (1989). "Binding activities of a repertoire of single immunoglobulin variable domains secreted from *Escherichia coli*," Nature, 341:544-546.
Garcia-Garcia et al., "Immune Signaling Kinases in Amyotrophic Lateral Sclerosis (ALS) and Frontotemporal Dementia (FTD)," Int. J. Mol. Sci. (2021) 22:13280, pp. 1-15.

* cited by examiner

A

B

C

METHODS AND AGENTS FOR TREATING ACUTE NEUROINFLAMMATORY INJURY

CROSS REFERENCE TO RELATED APPLICATIONS

This application is a national stage application under 35 U.S.C. § 371 of International Application No. PCT/US2020/043619, filed internationally on 24 Jul. 2020, which claims priority to Australian Provisional Application No. 2019902642 entitled "Methods and agents for treating acute neuroinflammatory injury" filed 25 Jul. 2019, the contents of which are incorporated herein by reference in their entirety.

INCORPORATION BY REFERENCE OF SEQUENCE LISTING

The present application is being filed along with a Sequence Listing in electronic format. The Sequence Listing is provided as a file entitled 229752008100SeqList.TXT, created Jan. 24, 2022, which is 15,258-15,370 bytes in size. The information in the electronic format of the Sequence Listing is incorporated by reference in its entirety.

FIELD OF THE INVENTION

This disclosure relates generally to methods and agents for treating acute neuroinflammatory injury, such as stroke (e.g. ischemic stroke or hemorrhagic stroke), hypoxic-ischemic brain injury, traumatic brain injury, subarachnoid hemorrhage and intracerebral hemorrhage. In particular, the present disclosure relates to the use of CD14 antagonist antibodies for treating acute neuroinflammatory injury.

BACKGROUND OF THE INVENTION

Stroke is a leading cause of death and disability in the world and is listed as the top neurological disease burden in developed countries. Stroke is caused by obstruction or rupture of cerebral vascular vessels. The interruption of cerebral blood flow leads to neural injury and irreversible long-term sensorimotor deficits. This damage is caused by energy depletion, excitotoxicity, peri-infarct depolarization, inflammation and programmed cell death. There are two common types of stroke: (i) ischemic stroke, which is caused by a temporary or permanent occlusion to blood flow to the brain, and accounts for 85% of stroke cases, and (ii) hemorrhagic stroke, which is caused by a ruptured blood vessel and accounts for the majority of the remaining cases. The most common cause of ischemic stroke is occlusion of the middle cerebral artery (the intra-cranial artery downstream from the internal carotid artery), which damages cerebrum. Such damage results in hemiplegia, hemi-anesthesia and, depending on the cerebral hemisphere damaged, either language or visuo-spatial deficits. Only about 50% of hemorrhagic stroke sufferers survive, and 85% of ischemic stroke victims survive. However, with complete recovery at only around 10%, the majority of stroke patients sustain long-term debilitating impairments to their physical, mental and social wellbeing.

One of the main factors in stroke being such a leading cause of death and disability is the scarcity of suitable and effective treatments. Outside of recanalization, there are no other treatments for stroke in the acute phase. For patients with ischemic stroke, early treatment to restore blood flow to the affected area of the brain can limit the extent of damage and increase the patient's chance of recovery. This treatment can include thrombolysis (e.g. by intravenous administration of tissue plasminogen activator) or thrombectomy, which involves physical removal of a clot from the brain. While thrombolysis applied up to 4.5 hours after the onset of symptoms has been shown to improve recovery, very few stroke sufferers are beneficiaries of this treatment, mostly due to delayed admission to hospital or an unknown time of onset. Also of concern is the fact that thrombolysis applied beyond 3 hours post-stroke has a significant associated risk of bleeding. There is therefore a short window of 3 to 4.5 hours post-stroke in which thrombolysis is generally applied. It is estimated that less than 15% of stroke sufferers who are admitted to hospital are therefore eligible to receive thrombolysis. The percentage of stroke sufferers who are eligible for thrombectomy is even less, at around 10%.

Accordingly, there remains a need for additional agents and methods for treating stroke and other acute neuroinflammatory injuries.

SUMMARY OF THE INVENTION

The present invention arises in part from the surprising determination that targeting Cluster of Differentiation 14 (CD14), such as by administration (e.g. systemic administration) of an anti-CD14 antagonist antibody, can treat stroke and prevent, reduce or ameliorate the associated symptoms of stroke, such as infarct size, functional decline, neurological deficit, and edema. Surprisingly, as demonstrated herein, targeting CD14 with just a single dose of an antagonist antibody at, for example, 6 hours post-stroke, significantly reduces neurological deficit, functional decline and infarct size. Conversely, an extended dosage regimen, such as over 7 days, is less effective.

Hypoxic neurons, such as resulting from stroke, generate many types of damage associated molecular patterns (DAMPs) that activate Toll-like receptors (TLRs) and their co-receptor CD14, located on microglia, monocytes, and peripheral macrophages (innate immune cells). Engaging the DAMP/CD14/ TLR axis activates microglia/macrophages and promotes pro-inflammatory cytokine release that mediates damage. Multiple TLRs are activated in neuronal injury by multiple DAMPs, each contributing to stroke outcome. However, many of these DAMP/TLR interactions require co-activation with CD14 for effective signaling. Without being bound by theory, it is proposed that targeting CD14 in the acute phase (e.g. up to 48 hours post-injury) or early subacute phase (e.g. up to 4 days post-injury) regulates DAMP driven neuroinflammation following stroke or other acute neuroinflammatory injury, thereby reducing the symptoms of the stroke or other acute neuroinflammatory injury. Conversely, it may be undesirable to target CD14 in the later subacute phase or chronic phase (i.e. after 4 days post-injury) as CD14+ immune cells may be important contributors to neurorepair and neuroregeneration in this period.

However, the outcome of attenuating the DAMP/CD14 TLR axis with an anti-CD14 antagonist antibody in the context of stroke or other acute neuroinflammatory injury, as demonstrated herein, was not at all predictable in view of previously-published studies. For example, modulation of CD14 by genetic ablation has been shown to result in larger infarcts and worse outcomes in mouse models of stroke (Janova et al., Glia, 2016, 64, 635-649).

That administration of just a single dose of anti-CD14 antagonist antibody 6 hours post-stroke is effective is not only surprising, it also has significant clinical implications. Most stroke patients will not be diagnosed until 6-12 hours post-stroke. Therefore, the earliest stroke intervention should be efficacious at a minimum of 6 hours post-stroke. Current thrombolytic treatments are only able to be used within 3 to 4.5 hours post-stroke due to the potential for a bleed in the brain after this time period. The use of an anti-CD14 antagonist antibody, which is effective 6 or more hours post-stroke, therefore represents a significant clinical improvement on current treatment of stroke, and further represents potential new treatments for other acute neuroinflammatory injuries, such as hypoxic-ischemic brain injury, traumatic brain injury, subarachnoid hemorrhage and intracerebral hemorrhage.

Accordingly, in one aspect, the present disclosure provides a method for treating acute neuroinflammatory injury in a human subject, comprising, consisting or consisting essentially of administering an effective amount of a CD14 antagonist antibody to the subject, wherein the antibody is administered to the subject up to 48 hours post-injury.

In another aspect, the disclosure provides a method for treating acute neuroinflammatory injury in a human subject, comprising, consisting or consisting essentially of systemically administering an effective amount of a CD14 antagonist antibody to the subject, wherein the antibody is administered alone. In some embodiments, the antibody is administered to the subject up to 48 hours post-injury.

Another aspect of the disclosure provides for treating acute neuroinflammatory injury in a human subject, comprising, consisting or consisting essentially of administering an effective amount of a CD14 antagonist antibody to the subject, wherein the antibody is administered as a single dose. In some embodiments, the antibody is administered to the subject up to 48 hours post-injury.

In a further aspect, the disclosure provides a method of treating acute neuroinflammatory injury in a human subject, comprising, consisting or consisting essentially of administering an effective amount of a CD14 antagonist antibody to the subject, wherein the CD14 antagonist antibody is selected from: (i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3); (ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (iii) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3). In some embodiments, the antibody is administered to the subject up to 48 hours post-injury.

In particular embodiments of the above methods, the antibody is administered to the subject up to 12, 18 or 24 hours post-injury. For example, the antibody may be administered to the subject between 2 and 48 hours, between 4 and 48 hours, between 6 and 48 hours, between 2 and 24 hours, between 4 and 24 hours, between 6 and 24 hours, between 2 and 18 hours, between 4 and 18 hours, between 6 and 18 hours, between 2 and 12 hours, between 4 and 12 hours, or between 6 and 12 hours post-injury. In a further embodiment, the antibody is administered as a single dose.

In some embodiments, the antibody is selected from: (i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3); (ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (iii) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

For example, the antibody may be selected from: (i) an antibody comprising: a VL domain that comprises, consists or consists essentially of the sequence: QSPASLAVSLGQRATISCRAS-ESVDSFGNSFMHWYQQKAGQPPKSSIYRAANLESGI-PARFSGSGSRTDFTLTI NPVEADD-VATYFCQQSYEDPWTFGGGTKLGNQ [SEQ ID NO: 1] (3C10 VL); and a VH domain that comprises, consists or consists essentially of the sequence: LVKPGGSLKLSCVASGFTFSSYAMSWVRQTPEKR-LEWVASISSGGTTYYPDNVKGRFTISRDNARNI-LYLQMSS LRSEDTAMYYCARGYYDYHYWGQGT-TLTVSS [SEQ ID NO: 2] (3C10 VH); (ii) an antibody comprising: a VL domain that comprises, consists or consists essentially of the sequence: QSPASLAVSLGQRATISCRAS-ESVDSYVNSFLHWYQQKPGQPPKLLIYRASNLQS GIPARFSGSGSRTDFTLTINPVEADD-VATYCCQQSNEDPTTFGGGTKLEIK [SEQ ID NO: 3] (28C5 VL); and a VH domain that comprises, consists or consists essentially of the sequence: LQQSGPGLVKP-SQSLSLTCTVTGYSITSDSAWNWIRQFPGNR-LEWMGYISYSGSTSYN PSLKSRISITRDTSKN QFFLQLNSVTTEDTATYYCVRGLR-FAYWGQGTLVTVSA [SEQ ID NO: 4] (28C5 VH); and (iii) an antibody comprising: a VL domain that comprises, consists or consists essentially of the sequence: QTPSSL-SASLGDRVTISCRASQDIK-NYLNWYQQPGGTVKVLIYYTSRLHSGVPSRFS GSGSGTDYSLTISNLEQE DFA-TYFCQRGDTLPWTFGGGTKLEIK [SEQ ID NO: 5] (18E12 VL); and a VH domain that comprises, consists or consists essentially of the sequence: LESGPGLVAPSQSL-SITCTVSGFSLTNYDISWIRQPPGKGLEW-LGVIWTSGGTNYNSAFMSRLSITKDNSESQVF LKMNGLQTDDTGIYYCVRGDGNFY-LYNFDYWGQGTTLTVSS [SEQ ID NO: 6] (18E12 VH). In particular embodiments, the antibody is humanized or chimeric. In one example, the antibody comprises a light chain and a heavy chain, wherein: the light chain comprises the amino acid sequence: METDTILLWVLLLWVPGSTG-DIVLTQSPASLAVSLGQRATISCRAS-ESVDSYVNSFLHWYQQKPGQPPKLLIYRA SNLQSGI-PARFSGSGSRTDFTLTINPVEADDVATYYCQQSNEDPY-TFGGGTKLEIKRTVAAPSVFIFPPSDEQLKS GTASVVCLLNNFYPREAKVQWKVD-NALQSGNSQESVTEQDSKDSTYSLSSTLTL-SKADYEKHKVYACEVTHQG LSSPVTKSFNRGEC [SEQ ID NO: 25]; and the heavy chain comprises the amino acid sequence: MKVLSLLYLLTAIPG-ILSDVQLQQSGPGLVKPSQSLSLTCTVTGYSITSD-SAWNWIRQFPGNRLEWMGYISYSGS TSYN-PSLKSRISITRDTSKNQFFLQLNSVTTEDTATYYCV RGLRFAYWGQGTLVTVSSASTKGPSVFPLAPCSRST SESTAALGCLVKDYFPEPVTVSWNSGALT-SGVHTFPAVLQSSGLYS-LSSVVTVPSSSLGTKTYTCNVDHKPSNTK VDKRVESKYGPPCPSCPAPE-FLGGPSVFLFPPKPKDTLMISRTPE-VTCVVVDVSQEDPEVQFNWYVDGVEVHNA KTKPREEQFN-STYRVVSVLTVLHQDWLNGKEYKCKVSNKGLPS-SIEKTISKAKGQPREPQVYTLPPSQEEMTKN QVSLT-CLVKGFYPSDIAVEWESNGQPEN-NYKTTPPVLDSDGSFFLY-SRLTVDKSRWQEGNVFSCSVMHEALHN HYTQKSLSLSLGK [SEQ ID NO: 26]. In particular examples, the antibody is the IC14 antibody.

In the above methods, the acute neuroinflammatory injury may be selected from, for example, stroke (e.g. ischemic stroke or hemorrhagic stroke), hypoxic-ischemic brain injury, traumatic brain injury, subarachnoid hemorrhage and intracerebral hemorrhage.

Also provided herein is a use of a CD14 antagonist antibody for the preparation of a medicament for treating acute neuroinflammatory injury (e.g. stroke, such as ischemic stroke or hemorrhagic stroke, hypoxic-ischemic brain injury, traumatic brain injury, subarachnoid hemorrhage or intracerebral hemorrhage) in a human subject, wherein the antibody is administered to the subject up to 48 hours post-injury.

In another aspect, provided is a use of a CD14 antagonist antibody for the preparation of a medicament for treating acute neuroinflammatory injury (e.g. stroke, such as ischemic stroke or hemorrhagic stroke, hypoxic-ischemic brain injury, traumatic brain injury, subarachnoid hemorrhage or intracerebral hemorrhage) in a human subject, wherein the medicament is formulated for systemic administration to the subject, and wherein the medicament does not contain an additional active agent. In one embodiment, the medicament is administered to the subject up to 48 hours post-injury.

Another aspect of the disclosure provides a use of a CD14 antagonist antibody for the preparation of a medicament for treating acute neuroinflammatory injury in a human subject, wherein the medicament is administered to the subject in a single dose. In one embodiment, the medicament is administered to the subject up to 48 hours post-injury.

In a further aspect, the present disclosure provides a use of a CD14 antagonist antibody for the preparation of a medicament for treating acute neuroinflammatory injury (e.g. stroke, such as ischemic stroke or hemorrhagic stroke, hypoxic-ischemic brain injury, traumatic brain injury, subarachnoid hemorrhage or intracerebral hemorrhage) in a human subject, wherein the antibody is selected from: (i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3); (ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (iii) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3). In one embodiment, the medicament is administered to the subject up to 48 hours post-injury.

In one example of the uses of the present disclosure, the antibody comprises a light chain and a heavy chain, wherein: the light chain comprises the amino acid sequence: METDTILLWVLLLWVPGSTGDI-VLTQSPASLAVSLGQRATISCRAS-ESVDSYVNSFLHWYQQKPGQPPKLLIYRA SNLQSGI-PARFSGSGSRTDFTLTINPVEADDVATYYCQQSNEDPY-TFGGGTKLEIKRTVAAPSVFIFPPSDEQLKS GTASVVCLLNNFYPREAKVQWKVD-NALQSGNSQESVTEQDSKDSTYSLSSTLTL-SKADYEKHKVYACEVTHQG LSSPVTKSFNRGEC [SEQ ID NO: 25]; and the heavy chain comprises the amino acid sequence: MKVLSLLYLLTAIPG-ILSDVQLQQSGPGLVKPSQSLSLTCTVTGYSITSD-SAWNWIRQFPGNRLEWMGYISYSGS TSYN-PSLKSRISITRDTSKNQFFLQLNSVTTEDTATYYC-VRGLRFAYWGQGTLVTVSSASTKGPSVFPLAPCSRST SESTAALGCLVKDYFPEPVTVSWNSGALT-SGVHTFPAVLQSSGLYS-LSSVVTVPSSSLGTKTYTCNVDHKPSNTK VDKRVESKYGPPCPSCPAPE-FLGGPSVFLFPPKPKDTLMISRTPE-VTCVVVDVSQEDPEVQFNWYVDGVEVHNA KTKPREEQFN-STYRVVSVLTVLHQDWLNGKEYKCKVSNKGLPS-SIEKTISKAKGQPREPQVYTLPPSQEEMTKN QVSLT-CLVKGFYPSDIAVEWESNGQPEN-NYKTTPPVLDSDGSFFLY-SRLTVDKSRWQEGNVFSCSVMHEALHN HYTQKSLSLSLGK [SEQ ID NO: 26]. In particular examples, the antibody is the IC14 antibody.

In some embodiment of the uses described above, the medicament is administered to the subject up to 12, 18 or 24 hours post-injury. In particular examples, the medicament is administered to the subject between 2 and 48 hours, between 4 and 48 hours, between 6 and 48 hours, between 2 and 24 hours, between 4 and 24 hours, between 6 and 24 hours, between 2 and 18 hours, between 4 and 18 hours, between 6 and 18 hours, between 2 and 12 hours, between 4 and 12 hours, or between 6 and 12 hours post-injury. In another example, the medicament is administered as a single dose.

BRIEF DESCRIPTION OF THE DRAWINGS

Embodiments of the disclosure are described herein, by way of non-limiting example only, with reference to the following drawings.

DETAILED DESCRIPTION OF THE INVENTION

1. Definitions

Figure 1:
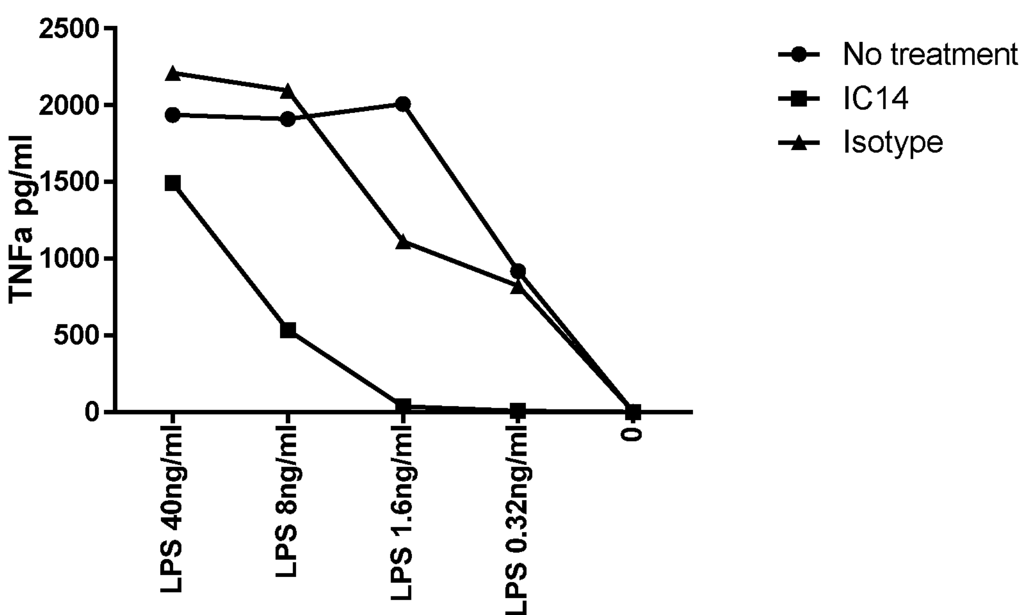
FIG. 1 demonstrates that anti-CD14 antibodies block LPS-dependent cytokine production. (A) Human microglia (from a single donor) pre-treated with IC14 show reduced TNFα in response to LPS stimulation. (B) Human peripheral blood mononuclear cells pre-treated with IC14 show a dose dependent reduction in IL-6 in response to LPS stimulation. (C) Murine RAW264.7 cells pre-treated with anti-CD14 biG53 mAb or its F(Ab')2 show a dose-dependent reduction in TNFα in response to LPS stimulation.
Figure 1:
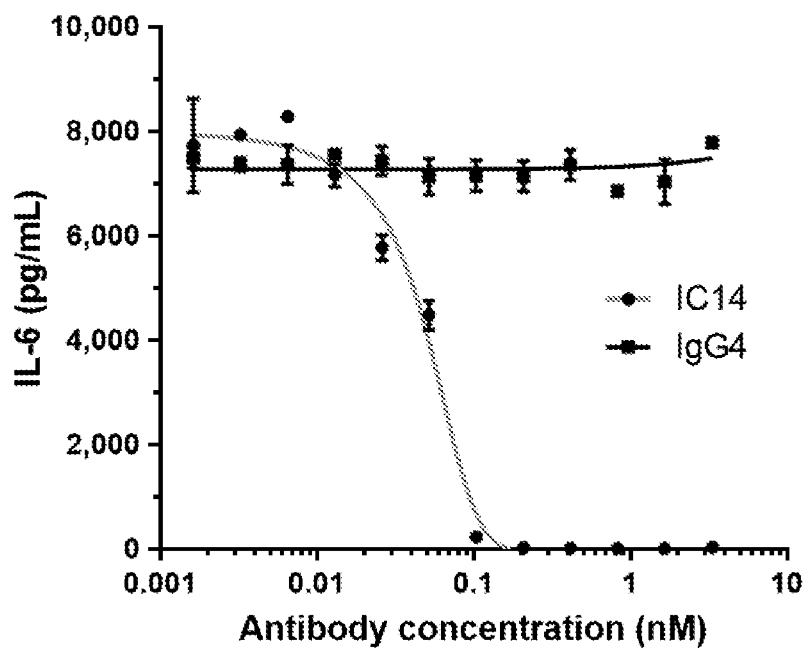
Figure 1:
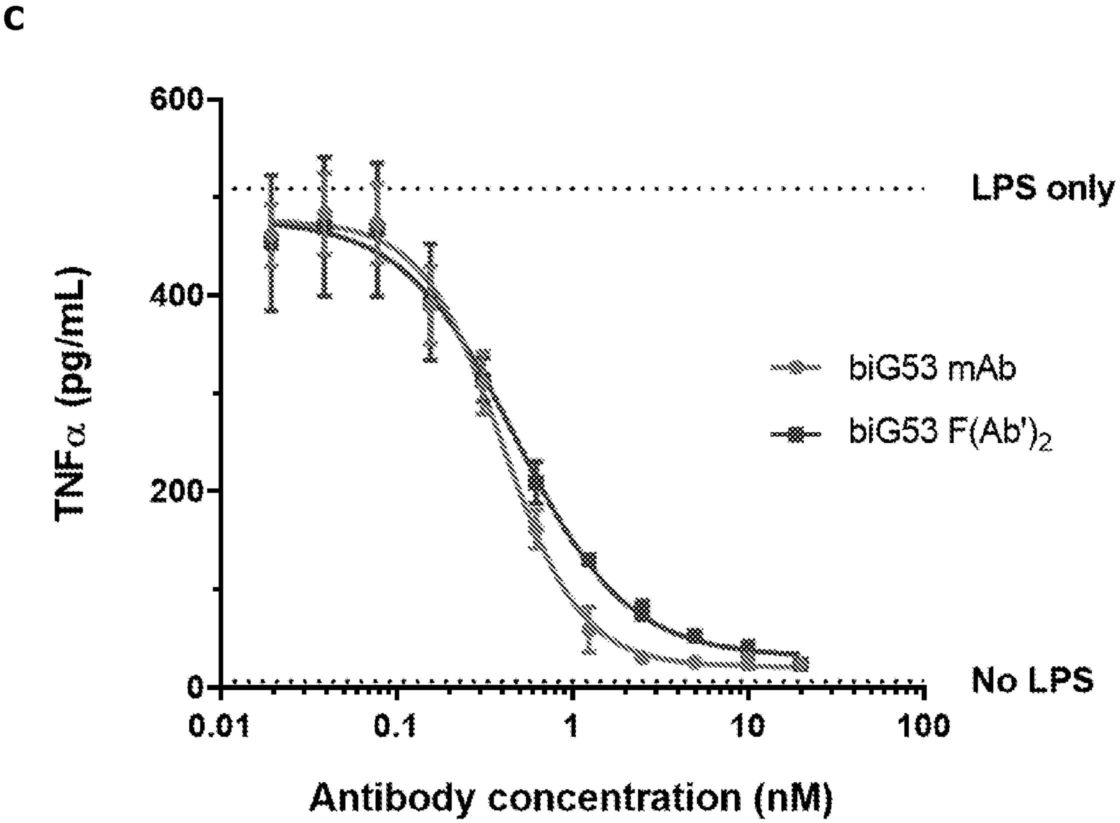

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

The terms "active agent" and "therapeutic agent" are used interchangeably herein and refer to agents that prevent, reduce or ameliorate at least one symptom of stroke or other acute neuroinflammatory injury.

As used herein, "acute neuroinflammatory injury" refers to an acute injury of the brain that is associated with a detrimental neuroinflammatory response, i.e. one that results in prolonged damage to the brain and loss of brain function without therapeutic intervention. Illustrative examples of acute neuroinflammatory injury include stroke (e.g. ischemic stroke or hemorrhagic stroke), hypoxic-ischemic brain injury, traumatic brain injury, subarachnoid hemorrhage (i.e. bleeding located underneath one of the protective layers of the brain known as the arachnoid layer, and into the space surrounding the brain) and intracerebral hemorrhage (i.e. bleeding within the brain). Symptoms of acute neuroinflammatory injury include, but are not limited to, hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting. The term "post-injury" with reference to a time period means the time period after the onset of the first symptom(s) of acute neuroinflammatory injury. Thus, for example, reference to "6 hours post-injury" means 6 hours after the onset of acute neuroinflammatory injury symptoms. As would be appreciated, when the neuroinflammatory injury is stroke, "post-stroke" and "post-injury" may be used interchangeably herein.

The terms "administration concurrently" or "administering concurrently" or "co-administering" and the like refer to the administration of a single composition containing two or more agents, or the administration of each agent as separate compositions and/or delivered by separate routes either contemporaneously or simultaneously or sequentially within a short enough period of time that the effective result is equivalent to that obtained when all such agents are administered as a single composition. By "simultaneously" is meant that the agents are administered at substantially the same time, and desirably together in the same formulation. By "contemporaneously" it is meant that the agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The agents may be administered in either order. The term "sequentially" as used herein means that the agents are administered in sequence, for example at an interval or intervals of minutes, hours, days or weeks. If appropriate the agents may be administered in a regular repeating cycle.

The term "alone" with reference to administration of a CD14 antagonist antibody or medicament comprising a CD14 antagonist antibody means that no other active agent is administered with the CD14 antagonist antibody or medicament to the subject during the course of treatment of the injury (e.g. stroke), i.e. the CD14 antagonist antibody or medicament comprising a CD14 antagonist antibody is not co-administered with another active agent.

The term "antagonist antibody" is used in the broadest sense, and includes an antibody that inhibits or decreases the biological activity of an antigen to which the antibody binds (e.g., CD14). For example, an antagonist antibody may partially or completely block interaction between a receptor (e.g., CD14) and a ligand (e.g., a DAMP or PAMP), or may practically decrease the interaction due to tertiary structure change or down regulation of the receptor. Thus, a CD14 antagonist antibody encompasses antibodies that bind to CD14 and that block, inhibit, nullify, antagonize, suppress, decrease or reduce (including significantly), in any meaningful degree, a CD14 agonist activity, including activation of downstream pathways such as Toll-like receptor (TLR) signaling pathways (e.g., TLR4 signaling pathway) and the TIR-domain-containing adapter-inducing IFN-β (TRIF) pathway, or elicitation of a cellular response (e.g., production of pro-inflammatory mediators including pro-inflammatory cytokines) to CD14 binding by a CD14 ligand (e.g., a DAMP or PAMP).

The term "antibody" herein is used in the broadest sense and specifically covers naturally occurring antibodies, monoclonal antibodies, polyclonal antibodies, multispecific antibodies (e.g., bispecific antibodies), antibody fragments, or any other antigen-binding molecule so long as they exhibit the desired immuno-interactivity. A naturally occurring "antibody" includes within its scope an immunoglobulin comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised specific CH domains (e.g., CH1, CH2 and CH3). Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of an immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g., IgG1 isotype, which carries L234A and L235A double mutations (IgG1-LALA)). The antibodies can be of any species, chimeric, humanized or human. In other embodiments, the antibody is a homomeric heavy chain antibody (e.g., camelid antibodies) which lacks the first constant region domain (CH1) but retains an otherwise intact heavy chain and is able to bind antigens through an antigen-binding domain. The variable regions of the heavy and light chains in the antibody-modular recognition domain (MRD) fusions will contain a functional binding domain that interacts with an antigen of interest.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four FRs whose sequences are widely conserved, connected by three CDRs or "hypervariable regions". The FRs adopt a β-sheet conformation and the CDRs may form loops connecting the β-sheet structure. The CDRs in each chain are held in their three-dimensional structure by the FRs and form together with the CDRs from the other chain the antigen binding site.

The term "antigen-binding portion" when used herein refer to the amino acid residues of an antibody which are responsible for antigen-binding generally, which generally comprise amino acid residues from the CDRs. Thus, "CDR" or "complementarity determining region" (also referred to as "hypervariable region") are used interchangeably herein to refer to the amino acid sequences of the light and heavy chains of an antibody which form the three-dimensional loop structure that contributes to the formation of an antigen binding site. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, 1987. *J. Mol. Biol.* 196: 901-917; Chothia et al., 1989. *Nature* 342: 877-883) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan (1995. *FASEB J.* 9: 133-139) and MacCallum (1996. *J. Mol. Biol.* 262(5): 732-745). Still other CDR boundary definitions may not strictly follow one of these systems, but will nonetheless overlap with the Kabat CDRs, although they may be shortened or lengthened in light of prediction or experimental findings that particular residues or groups of residues or even entire CDRs do not significantly impact antigen binding.

As used herein, the term "framework region" or "FR" refers to the remaining sequences of a variable region minus the CDRs. Therefore, the light and heavy chain variable domains of an antibody comprise from N- to C-terminus the domains FR1, CDR1, FR2, CDR2, FR3, CDR3, and FR4. CDRs and FRs are typically determined according to the standard definition of Kabat, E. A., et al., Sequences of Proteins of Immunological Interest, 5th ed., Public Health Service, National Institutes of Health, Bethesda, Md. (1991) and/or those residues from a "hypervariable loop".

As used herein, the terms "light chain variable region" ("VL") and "heavy chain variable region" (VH) refer to the regions or domains at the N-terminal portion of the light and heavy chains respectively which have a varied primary amino acid sequence for each antibody. The variable region of an antibody typically consists of the amino terminal domain of the light and heavy chains as they fold together to form a three-dimensional binding site for an antigen. Several subtypes of VH and VL, based on structural similarities, have been defined, for example as set forth in the Kabat database.

The term "chimeric antibody" refers to antibodies that comprise heavy and light chain variable region sequences from one species and constant region sequences from another species, such as antibodies having murine heavy and light chain variable regions linked to human constant regions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Thus, the FRs and CDRs of a humanized antibody need not correspond precisely to the parental (i.e., donor) sequences, e.g., a donor antibody CDR or the consensus framework may be mutagenized by substitution, insertion, and/or deletion of at least one amino acid residue so that the CDR or FR at that site does not correspond to either the donor antibody or the consensus framework. Typically, such mutations, however, will not be extensive and will generally avoid "key residues" involved in binding to an antigen. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, for example, Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will generally comprise at least a portion of an immunoglobulin constant region (Fc), typically that of a human immunoglobulin. For further details, see Jones et al. (1986. *Nature* 321:522-525), Riechmann et al. (1988. *Nature* 332:323-329) and Presta (1992. *Curr. Op. Struct. Biol.* 2:593-596). A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well known in the art. As used herein, the term "key residue" refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, "Vernier" zone refers to a subset of framework residues that may adjust CDR structure and fine-tune the fit to antigen as described by Foote and Winter (1992. *J. Mol. Biol.* 224: 487-499). Vernier zone residues form a layer underlying the CDRs and may impact on the structure of CDRs and the affinity of the antibody.

As used herein, the term "canonical" residue refers to a residue in a CDR or framework that defines a particular canonical CDR structure as defined by Chothia et al. (1987. *J. Mol. Biol.* 196: 901-917; 1992. *J. Mol. Biol.* 227: 799-817), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs to an "acceptor antibody". In some embodiments, the donor antibody is an antibody from a species different from the antibody from which the FRs are obtained or derived. In the context of a humanized antibody, the term "donor antibody" refers to a non-human antibody providing one or more CDRs.

As used herein, the terms "acceptor" and "acceptor antibody" refer to an antibody providing at least 80%, at least 85%, at least 90%, at least 95%, at least 98%, or 100% of the amino acid sequences of one or more of the FRs. In some embodiments, the term "acceptor" refers to the antibody amino acid sequence providing the constant region(s). In other embodiments, the term "acceptor" refers to the antibody amino acid sequence providing one or more of the FRs and the constant region(s). In specific embodiments, the term "acceptor" refers to a human antibody amino acid sequence that provides at least 80%, preferably, at least 85%, at least 90%, at least 95%, at least 98%, or 100% of the amino acid sequences of one or more of the FRs. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, for example, derived or obtained from a germline antibody gene, a mature antibody gene, a functional antibody (e.g., antibodies well-known in the art, antibodies in development, or antibodies commercially available).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3" antibody fragment. Throughout the specification, complementarity determining regions ("CDR") are defined according to the Kabat definition unless specified otherwise. The Kabat definition is a standard for numbering the residues in an antibody and it is typically used to identify CDR regions (Kabat et al., (1991), 5th edition, NIH publication No. 91-3242).

Antigen binding can be performed by "fragments" or "antigen-binding fragments" of an intact antibody. Herein, both terms are used interchangeably. Examples of binding fragments encompassed within the term "antibody fragment" of an antibody include a Fab fragment, a monovalent fragment consisting of the VL, VH, CL and CH1 domains; a F(ab')2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989. *Nature* 341:544-546), which consists of a VH domain; and an isolated complementary determining region (CDR). In a particular embodiment, the antibody of the present disclosure is an antigen-binding fragment that lacks all or a portion of the Fc region.

A "single chain variable Fragment (scFv)" is a single protein chain in which the VL and VH regions pair to form monovalent molecules (known as single chain Fv (scFv); see, e.g., Bird et al., 1988. *Science* 242:423-426; and Huston et al., 1988. *Proc. Natl. Acad. Sci.* 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "monoclonal antibody" and abbreviations "MAb" and "mAb", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method. Monoclonal antibodies may be produced, for example, by a single clone of antibody-producing cells, including hybridomas. The term "hybridoma" generally refers to the product of a cell-fusion between a cultured neoplastic lymphocyte and a primed B- or T-lymphocyte which expresses the specific immune potential of the parent cell.

An antibody "that binds" an antigen of interest (e.g., CD14) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody, oligopeptide or other organic molecule to its particular target protein as determined, for example, by fluorescence activated cell sorting (FACS) analysis, enzyme-linked immunosorbent assay (ELISA), immunoprecipitation or radioimmunoprecipitation (RIA). Thus, an antibody that antagonizes CD14 suitably inhibits or decreases production of pro-inflammatory mediators, including pro-inflammatory cytokines/chemokines. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The specific region of the antigen to which the antibody binds is typically referred to as an "epitope". The term "epitope" broadly includes the site on an antigen which is specifically recognized by an antibody or T-cell receptor or otherwise interacts with a molecule. Generally epitopes are of active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "effective amount", in the context of treating a condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the age, health and physical condition of the individual to be treated and whether symptoms of disease are apparent, the taxonomic group of individual to be treated, the formulation of the composition, the assessment of the medical situation, and other relevant factors. Optimal dosing schedules can be calculated from measurements of drug accumulation in the body of the subject. Optimum dosages may vary depending on the relative potency in an individual subject, and can generally be estimated based on EC50 values found to be effective in in vitro and in vivo animal models. Persons of ordinary skill can easily determine optimum dosages, dosing methodologies and repetition rates. It is expected that the amount will fall in a relatively broad range that can be determined through routine trials.

As used herein, the term "immune cell" refers to a cell belonging to the immune system. Immune cells include cells of hematopoietic origin such as but not limited to T lymphocytes (T cells), B lymphocytes (B cells), natural killer (NK) cells, granulocytes, neutrophils, macrophages, monocytes, dendritic cells, and specialized forms of any of the foregoing, e.g., plasmacytoid dendritic cells, Langerhans cells, plasma cells, natural killer T (NKT) cells, T helper cells, and cytotoxic T lymphocytes (CTL).

The terms "inhibit", "inhibiting", "decrease" or "decreasing and the like, in relation to "the production of pro-inflammatory mediators" by cells as used herein refers to at least a small but measurable reduction in the level or amount of pro-inflammatory mediator/s produced by a peripheral cell. In embodiments, the production of the pro-inflammatory mediator by a cell is inhibited or decreased by at least 20% over non-treated controls; in more embodiments, the inhibition or decrease is at least 50%; in still more embodiments, the inhibition or decrease is at least 70%, and in embodiments, the inhibition or decrease is at least 80%. Such reductions in pro-inflammatory mediator production are capable of reducing the deleterious effects of an inflammatory mediator cascade in in vivo embodiments.

A suitable in vitro assay (e.g. ELISA, RT-PCR) can be used to evaluate the efficacy of a CD14 antagonist antibody in inhibiting or decreasing the production of pro-inflammatory mediators by a peripheral cell. For example, competitive RT-PCR techniques can be used to measure the levels of cytokine mRNA obtained from within a cell, and the levels of expressed cytokine released from the cell can be measured by sandwich ELISA using, for example, one or more monoclonal antibodies which specifically bind to a particular cytokine. In vivo screening can also be performed by following procedures well known in the art. For example, a CD14 antagonist antibody is administered to an animal model (e.g., a mouse) and blood is collected to assess the levels of various cytokines. The skilled person would be well versed in the techniques available for the measurement of cytokine production. Based on the results, an appropriate dosage range and systemic administration route can also be determined.

The term "ischemia" as used herein refers to an inadequate or stopped flow of blood to a part of the body, caused by constriction or blockage of the blood vessels supplying it.

The term "hypoxic-ischemic brain injury" refers to an absolute or relative shortage of oxygen or blood supply to the brain, with resultant damage or dysfunction of cerebral tissue. Hypoxic-ischemic brain injury can be the result of various diseases, insults or injuries, including, for example, cardiac arrest, respiratory ischemic stroke, head trauma, strangulation or poisoning (e.g. carbon monoxide poisoning or drug overdose). Severe or prolonged cerebral ischemia will result in unconsciousness, brain damage or death (e.g. neuronal damage), mediated by the ischemic cascade.

By "isolated" is meant material that is substantially or essentially free from components that normally accompany it in its native state.

The term "ligand", as used herein, refers to any molecule which is capable of binding a receptor.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The term "pro-inflammatory mediator" means an immunoregulatory agent that favors inflammation. Such agents include, cytokines such as chemokines, interleukins (IL), lymphokines, and tumor necrosis factor (TNF) as well as growth factors. In specific embodiments, the pro-inflammatory mediator is a "pro-inflammatory cytokine". Typically, pro-inflammatory cytokines include IL-1$\alpha$, IL-1$\beta$, IL-6, and TNF-$\alpha$, which are largely responsible for early responses. Other pro-inflammatory mediators include LIF, IFN-$\gamma$, IFN-$\beta$, IFN-$\alpha$, OSM, CNTF, TGF-$\beta$, GM-CSF, TWEAK, IL-11, IL-12, IL-15, IL-17, IL-18, IL-19, IL-20, IL-8, IL-16, IL-22, IL-23, IL-31 and IL-32 (Tato et al., 2008. *Cell* 132:900; *Cell* 132:500, *Cell* 132:324). Pro-inflammatory mediators may act as endogenous pyrogens (IL-1, IL-6, IL-17, TNF-$\alpha$), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. In specific embodiments, the term "pro-inflammatory cytokine" relates to TNF-$\alpha$, IL-1 $\alpha$, IL-6, IFN$\beta$, IL-1$\beta$, IL-8, IL-17 and IL-18.

As used herein, "stroke" refers loss of brain function(s), usually rapidly developing, that is due to a disturbance in blood supply to the brain or brainstem. The disturbance can be ischemia (lack of blood) caused by, e.g., thrombosis or embolism, or can be due to a hemorrhage. In some examples, the loss of brain function is accompanied by neuronal cell death. In one example, the stroke is caused by a disturbance or loss of blood from to the cerebrum or a region thereof. Stroke is a neurological deficit of cerebrovascular cause that persists beyond 24 hours or is interrupted by death within 24 hours (as defined by the World Health Organization). Symptoms of stroke include hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting. The term "post-stroke" with reference to a time period means the time period after the onset of the first symptom(s) of stroke. Thus, for example, reference to "6 hours post-stroke" means 6 hours after the onset of stroke symptoms.

As used herein, the term "systemic administration" or "administered systemically" or "systemically administered" means introducing an agent into a subject outside of the central nervous system. Systemic administration encompasses any route of administration other than direct administration to the spine or brain. As such, it is clear that intrathecal and epidural administration as well as cranial injection or implantation, are not within the scope of the terms "systemic administration", "administered systemically" or "systemically administered". An agent (e.g. an antibody) or pharmaceutical composition as described herein can be systemically administered in any acceptable form such as in a tablet, liquid, capsule, powder, or the like; by intravenous, intraperitoneal, intramuscular, subcutaneous or parenteral injection; by transdermal diffusion or electrophoresis; and by minipump or other implanted extended release device or formulation. According to some embodiments, systemic administration is carried out by a route selected from the group consisting of intraperitoneal, intravenous, subcutaneous and intranasal administration, and combinations thereof.

Reference herein to a "single dose" of a CD14 antagonist antibody means that the subject is administered only one dose, e.g. in one bolus injection or one discrete infusion, of the antibody following an acute neuroinflammatory injury. In the event that the subject suffers a further acute neuroinflammatory injury, the subject may be administered a single dose of the antibody for that further acute neuroinflammatory injury. Thus, reference to a single dose means that the subject receives only one dose of the antibody for each instance of acute neuroinflammatory injury.

The terms "subject", "patient" and "individual" used interchangeably herein, refer to any subject, particularly a vertebrate subject, and even more particularly a mammalian subject, (e.g. human) that has suffered an acute neuroinflammatory injury.

The term "traumatic brain injury" or "TBI" refers to refers to brain injury caused by external physical trauma. Non-limiting examples of incidences resulting in TBI include falls, vehicle collisions, sports collisions, and combats. The term includes both mild and severe TBI including closed-head injuries, concussions or contusions and penetrating head injuries.

As used herein, the terms "treatment", "treating", and the like, refer to obtaining a desired pharmacologic and/or physiologic effect in a subject in need of treatment, that is, a subject who has suffered an acute neuroinflammatory injury. By "treatment" is meant; ameliorating or preventing one or more symptoms of acute neuroinflammatory injury; ameliorating or preventing neuronal damage or neurological deficit; and/or improving or prolonging quality of life. Reference to "treatment", "treat" or "treating" does not necessarily mean to reverse or prevent any or all symptoms of acute neuroinflammatory injury, or reverse or prevent neuronal damage or neurological deficit. For example, the subject may ultimately suffer prolonged neurological deficit, but the extent of the deficit is reduced and/or the quality of life is improved compared to the extent of the deficit or the quality of life without treatment.

As used herein, "up to" in reference to a time period post-injury or post-stroke for administration of a CD14 antagonist antibody means that the subject is not administered any CD14 antagonist antibody beyond this time during treatment of the injury (e.g. stroke). Thus, for example, reference to administration of a CD14 antagonist antibody to a subject "up to 48 hours post-injury" means that the CD14 antagonist antibody may be administered to the subject at any time from 0-48 hours post-injury, but at no point after 48 hours. The administration may include one or more doses of CD14 antagonist antibody, but no dose will be administered after the designated time period, e.g. 48 hours post-injury. However, it is understood that if the subject then suffers a further acute neuroinflammatory injury, the subject may be administered a CD14 antagonist antibody for that further acute neuroinflammatory injury in the time period defined.

Each embodiment described herein is to be applied mutatis mutandis to each and every embodiment unless specifically stated otherwise.

2. Compositions and Methods for Treating Neuroinflammatory Injury

The present disclosure provides methods, uses and compositions that include a CD14 antagonist antibody for treating acute neuroinflammatory injury.

2.1 CD14 Antagonist Antibodies

The present disclosure contemplates any CD14 antagonist antibody that binds to CD14 (e.g. mCD14 or sCD14) and blocks the binding of a DAMP or PAMP to CD14 and/or that binds to CD14 and inhibits or decreases a CD14 agonist-mediated response resulting in the production of pro-inflammatory mediators, including the production of pro-inflammatory cytokines. In some embodiments, a CD14 antagonist antibody of the present invention inhibits binding of a CD14 agonist, suitably a DAMP or PAMP, to CD14 thus inhibiting or decreasing the production of pro-inflammatory cytokines. In illustrative examples of this type, the CD14 antagonist antibody is selected from the 3C10 antibody that binds an epitope comprised in at least a portion of the region from amino acid 7 to amino acid 14 of human CD14 (van Voohris et al., 1983. *J. Exp. Med.* 158: 126-145; Juan et al., 1995. *J. Biol. Chem.* 270(29): 17237-17242), the MEM-18 antibody that binds an epitope comprised in at least a portion of the region from amino acid 57 to amino acid 64 of CD14 (Bazil et al., 1986. *Eur. J. Immunol.* 16(12):1583-1589; Juan et al., 1995. *J. Biol. Chem.* 270(10): 5219-5224), the 4C1 antibody (Adachi et al., 1999. *J. Endotoxin Res.* 5: 139-146; Tasaka et al., 2003. *Am. J. Respir. Cell. Mol. Biol.;* 2003. 29(2): 252-258), as well as the 28C5 and 23G4 antibodies that inhibit binding of LPS and suppress production of pro-inflammatory cytokines, and the 18E12 antibody that partly inhibits binding of LPS and suppresses production of pro-inflammatory cytokines (U.S. Pat. Nos. 5,820,858, 6,444,206 and 7,326,569 to Leturcq et al.). In some embodiments, a CD14 antagonist antibody of the present disclosure inhibits binding of CD14 to a TLR such as TLR4, thereby blocking CD14-agonist mediated response, illustrative examples of which include the F1024 antibody disclosed in International Publication WO2002/42333. Each of the above references relating to CD14 antagonist antibodies is incorporated herein by reference in its entirety. The CD14 antagonist antibody may be a full-length immunoglobulin antibody or an antigen-binding fragment of an intact antibody, representative examples of which include a Fab fragment, a F(ab')2 fragment, an Fd fragment consisting of the VH and CH1 domains, an Fv fragment consisting of the VL and VH domains of a single arm of an antibody, a single domain antibody (dAb) fragment (Ward et al., 1989. *Nature* 341: 544-546), which consists of a VH domain; and an isolated CDR. Suitably, the CD14 antagonist antibody is a chimeric, humanized or human antibody.

In some embodiments, the CD14 antagonist antibody is selected from the antibodies disclosed in U.S. Pat. No. 5,820,858:

(1) an antibody comprising:

a VL domain comprising, consisting or consisting essentially of the sequence: QSPASLAVSLGQRATISC RASESVDSFGNSFMH WYQQKAGQPPKSSIY RAANLES GIPARFSGSGSRTDFTLTINPVEADDVATYFC QQSYEDPWT FGGGTKLGNQ [SEQ ID NO: 1] (3C10 VL); and a VH domain comprising, consisting or consisting essentially of the sequence: LVKPGGSLKLSCVASGFTFS SYAMS WVRQTPEKRLEWVA SISSGGTTYYPDNVKG RFTISRDNARNILYLQMSSLRSEDTAMYYCAR GYYDYHY WGQGTTLTVSS [SEQ ID NO: 2] (3C10 VH);

(2) an antibody comprising:

a VL domain comprising, consisting or consisting essentially of the sequence: QSPASLAVSLGQRATISC RASESVDSYVNSFLH WYQQKPGQPPKLLIY RASNLQS GIPARFSGSGSRTDFTLTINPVEADDVATYCC QQSNEDPTT FGGGTKLEIK [SEQ ID NO: 3] (28C5 VL); and a VH domain comprising, consisting or consisting essentially of the sequence: LQQSGPGLVKPSQSLSLTCTVTGYSIT SDSAWN WIRQFPGNRLEWMG YISYSGSTSYNPSLKS RISITRDTSKNQFFLQLNSVTTEDTATYYCVR GLRFAY WGQGTLVTVSA [SEQ ID NO: 4] (28C5 VH); and (3) an antibody comprising:

a VL domain comprising, consisting or consisting essentially of the sequence: QTPSSLSASLGDRVTISC RASQDIKNYLN WYQQPGGTVKVLIY YTSRLHS GVPSRFSGSGSGTDYSLTISNLEQEDFATYFC QRGDTLPWT FGGGTKLEIK [SEQ ID NO: 5] (18E12 VL); and a VH domain comprising, consisting or consisting essentially of the sequence: LESGPGLVAPSQSLSITCTVSGFSLT NYDIS WIRQPPGKGLEWLG VIWTSGGTNYNSAFMS RLSITKDNSESQVFLKMNGLQTDDTGIYYCVR GDGNFYLYNFDY WGQGTTLTVSS [SEQ ID NO: 6] (18E12 VH);

Also contemplated are antibodies that comprise the VL and VH CDR sequences of the above antibodies, representative embodiments of which include:

(1) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10

L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);

(2) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (3) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

In some embodiments, the CD14 antagonist antibody is humanized. In illustrative examples of this type, the humanized CD14 antagonist antibodies suitably comprise a donor CDR set corresponding to a CD14 antagonist antibody (e.g., one of the CD14 antagonist antibodies described above), and a human acceptor framework. The human acceptor framework may comprise at least one amino acid substitution relative to a human germline acceptor framework at a key residue selected from the group consisting of: a residue adjacent to a CDR; a glycosylation site residue; a rare residue; a canonical residue; a contact residue between heavy chain variable region and light chain variable region; a residue within a Vernier zone; and a residue in a region that overlaps between a Chothia-defined VH CDR1 and a Kabat-defined first heavy chain framework. Techniques for producing humanized mAbs are well known in the art (see, for example, Jones et al., 1986. *Nature* 321: 522-525; Riechmann et al. 1988. *Nature* 332:323-329; Verhoeyen et al., 1988. *Science* 239: 1534-1536; Carter et al., 1992. *Proc. Natl. Acad. Sci. USA* 89: 4285-4289; Sandhu, J S., 1992. *Crit. Rev. Biotech.* 12: 437-462, and Singer et al., 1993. *J. Immunol.* 150: 2844-2857). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al. (1991. *Biotechnology* 9:266-271) and Verhoeyen et al. (1988 supra). Generally, those human FR amino acid residues that differ from their murine counterparts and are located close to or touching one or more CDR amino acid residues would be candidates for substitution.

In a preferred embodiment, the CD14 antagonist antibody is the IC14 antibody (Axtelle et al., 2001. *J. Endotoxin Res.* 7: 310-314; and U.S. Pat. Appl. No. 2006/0121574, which are incorporated herein by reference in their entirety) or an antigen-binding fragment thereof. The IC14 antibody is a chimeric (murine/human) monoclonal antibody that specifically binds to human CD14. The murine parent of this antibody is 28C5 noted above (see, U.S. Pat. Nos. 5,820,858, 6,444,206 and 7,326,569 to Leturcq et al., and Leturcq et al., 1996. *J. Clin. Invest.* 98: 1533-1538). The IC14 antibody comprises a VL domain and a VH domain, wherein:

```
the VL domain comprises the amino acid sequence:
                                   [SEQ ID NO: 25]
METDTILLWVLLLWVPGSTGDIVLTQSPASLAVSLGQRATISCRASESVD

SYVNSFLHWYQQKPGQPPKLLIYRASNLQSGIPARFSGSGSRTDFTLTIN

PVEADDVATYYCQQSNEDPYTFGGGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC;
and

the VH domain comprises the amino acid sequence:
                                   [SEQ ID NO: 26]
MKVLSLLYLLTAIPGILSDVQLQQSGPGLVKPSQSLSLTCTVTGYSITSD

SAWNWIRQFPGNRLEWMGYISYSGSTSYNPSLKSRISITRDTSKNQFFLQ

LNSVTTEDTATYYCVRGLRFAYWGQGTLVTVSSASTKGPSVFPLAPCSRS

TSESTAALGCLVKDYFPEPVTVSWNSGALTSGVHTFPAVLQSSGLYSLSS

VVTVPSSSLGTKTYTCNVDHKPSNTKVDKRVESKYGPPCPSCPAPEFLGG

PSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHYT

QKSLSLSLGK.
```

Additional antagonist antibodies of CD14 suitable for use in the treatment of neuroinflammatory injury, such as stroke or ischemic brain injury, can be identified by methods well known to those skilled in the art. These methods generally comprise determining whether an antibody is capable of directly antagonizing CD14. For example, the methods may involve determining whether an antibody is capable of inhibiting or decreasing the amount or agonist activity of CD14, wherein the ability to inhibit or decrease the amount or agonist activity of CD14 indicates that the antibody may be suitable for use in treating stroke or ischemic brain injury as described herein. In some embodiments, the antibody is contacted with CD14, or a cell that expresses CD14 on its surface, or a nucleic acid sequence from which CD14 is expressed, suitably in the presence of a CD14 agonist such as a DAMP or PAMP, wherein a decrease in the amount or agonist activity of CD14 in the presence of the agonist, when compared to a control, indicates that the antibody binds to CD14 and directly antagonizes CD14. A decrease or inhibition of CD14 agonist activity, includes for example inhibiting, or decreasing activation of downstream pathways such as TLR signaling pathways (e.g., TLR4 signaling pathway) and the TRIF pathway, or elicitation of a cellular response (e.g., production of pro-inflammatory mediators including pro-inflammatory cytokines).

These methods may be carried out in vivo, ex vivo or in vitro. In particular, the step of contacting an antibody with CD14 or with a cell that expresses CD14 on its surface (e.g., immune cells) may be carried out in vivo, ex vivo or in vitro. The methods may be carried out in a cell-based or a cell-free system. For example, the method may comprise a step of contacting a cell expressing CD14 on its surface with an antibody and determining whether the contacting of the cell with the antibody leads to a decrease in the amount or agonist activity of CD14. In such a cell-based assay, the CD14 and/or the antibody may be endogenous to the host cell, may be introduced into a host cell or tissue, may be introduced into the host cell or tissue by causing or allowing the expression of an expression construct or vector or may be introduced into the host cell by stimulating or activating expression from an endogenous gene in the cell. In such a cell-based method, the amount of activity of CD14 may be assessed in the presence or absence of an antibody in order to determine whether the agent is altering the amount of CD14 in the cell, such as through regulation of CD14 expression in the cell or through destabilization of CD14 protein within the cell, or altering the CD14 agonist activity of the cell. The presence of a lower CD14 agonist activity or a decreased amount of CD14 on the cell surface in the presence of the antibody indicates that the antibody may be a suitable antagonist of CD14 for use in accordance with the present disclosure.

In some examples, it is further determined whether the antibody lacks substantial or detectable binding to another cellular component, suitably a binding partner of CD14, such as a CD14 binding partner that is either secreted (e.g., MD2) or located on the cell membrane (e.g., TLR4), to thereby determine that the antibody is a specific antagonist of CD14. In a non-limiting example of this type, the antibody is contacted in the presence of a CD14 agonist such as a DAMP or PAMP (1) with a wild-type cell that expresses CD14 on its surface (e.g., an immune cell such a macrophage), and (2) with a CD14 negative cell (e.g., an immune cell that is the same as in (1) but has a loss of function in the CD14 gene). If the antibody inhibits a CD14 agonist activity of the wild-type cell but not of the CD14 negative cell, this indicates that the antibody is a CD14 specific antagonist. Cells of this type may be constructed using routine procedures or animals.

In other examples, potential CD14 antagonist antibodies are assessed in vivo, such as, for example, in an animal model. In such an in vivo model, the effects of the antibody may be assessed in the circulation (e.g., blood), or in other organs such as the liver, kidney or heart. In particular examples, the models of ischemia are used to assess the activity of the antibody.

Exemplary antagonist antibodies of CD14 effect a decrease in CD14 activity or levels of at least 5%, at least 10%, at least 25%, at least 50%, at least 60%, at least 75%, or at least 85% or more compared to in the absence of the antibody. In some examples, the antibody may result in a decrease in CD14 agonist activity or levels such that the agonist activity or level of CD14 is no longer detectable in the presence of the antibody. Such a decrease may be seen in the sample being tested or, for example where the method is carried out in an animal model, in particular tissue from the animal such as in the circulation or other organs such as the liver, kidney or heart.

Preferably, the antibody is a specific antagonist of CD14 as described above. However, this does not mean that a specific antagonist of CD14 has a complete absence of off-target antagonistic activity. In this regard, the specific antagonist of CD14 may have negligible or a minor direct binding and effect on other cellular components, such that the antagonism of the activity, signaling or expression of a non-CD14 cellular component, is less than less than 15%, less than 10%, less than 5%, less than 1%, or less than 0.1% of the direct binding and effect of that agent on the activity, signaling or expression of CD14.

Levels or amounts of CD14 may be measured by assessing expression of the CD14 gene. Gene expression may be assessed by looking at mRNA production or levels or at protein production or levels. Expression products such as mRNA and proteins may be identified or quantified by methods known in the art. Such methods may utilize hybridization to specifically identify the mRNA of interest. For example such methods may involve PCR or real-time PCR approaches. Methods to identify or quantify a protein of interest may involve the use of antibodies that bind that protein. For example, such methods may involve western blotting. Regulation of CD14 gene expression may be compared in the presence and absence of an antibody. Thus, antibodies can be identified that decrease CD14 gene expression compared to the level seen in the absence of the antibody. Such antibodies may be suitable antagonists of CD14 in accordance with the present disclosure.

The methods for identifying suitable antagonist antibodies for use in accordance with the present disclosure may assess the agonist activity of CD14. For example, such a method may be carried out using peripheral blood mononuclear cells. Such cells will produce cytokines such as IL-1 α, IL-6, TNF-α, IFN-β, IL-1β, IL-17 and IL-8 on response to stimulation with, for example, LPS. Methods may therefore comprise combining peripheral blood mononuclear cells with the antibody or a vehicle and adding LPS. The cells may then be incubated for an amount of time (e.g., 24 hours) to allow the production of pro-inflammatory mediators such as cytokines. The level of cytokines such as IL-1α, IL-6, TNF-α, IFN-β, IL-1β, IL-17 and IL-8 produced by the cells in that time period can then be assessed. If the antibody has anti-CD14 properties, then the production of such cytokines should be reduced compared to the vehicle-treated cells.

2.2 Ancillary Agents and Interventions

The CD14 antagonist antibody may administered alone or in combination with other active agents (also referred to as "ancillary agents") or other interventions. In one example, the antagonist antibody is administered in combination with a thrombolytic agent, such as a tissue plasminogen activator (tPA, e.g. alteplase, desmoteplase, tenecteplase or reteplase), streptokinase, urokinase, plasmin and microplasmin. Other ancillary agents include neuroprotective agents such as, but not limited to, NMDA antagonists (e.g. NA-1), anti-CD49d antibodies (e.g. natalizumab), NXY-059, and edavarone; neurorepair agents such as stem cells, pifithrin-α, bone morphogenetic protein 7 (BMP7), brain-derived neurotrophic factor (BDNF), glial cell line-derived neurotrophic factor (GDNF), epidermal growth factor (EGF), basic fibroblast growth factor (bFGF) and cocaine- and amphetamine-regulated transcript (CART); antiplatelet agents such as aspirin; and anticoagulant agents such as heparin, dabigatran, apixaban, edoxaban and rivaroxaban. In another example, administration of the antibody is in conjunction with interventions such as thrombectomy, therapeutic hypothermia, remote ischemic preconditioning, and/or extracranial or intracranial sonothrombolysis.

When combination therapy is desired, the CD14 antagonist antibody is administered separately, simultaneously or sequentially with one or more ancillary agents or interventions. In some embodiments, this may be achieved by administering systemically a single composition or pharmacological formulation that includes both types of agent, or by administering two separate compositions or formulations at the same time, wherein one composition includes the CD14 antagonist antibody and the other the ancillary agent. In other embodiments, the treatment with the CD14 antagonist antibody may precede or follow the treatment with the ancillary agent by intervals ranging from minutes to hours or even days or weeks. For example, neurorepair agents may be administered hours, days or weeks after administration of the CD14 antagonist antibody. Conversely, thrombolytic agents may be administered before or at the same time as the CD14 antagonist antibody.

In some situations, the antibody and ancillary agent are administered within about 1-12 hours of each other or within about 2-6 hours of each other. In other situations, it may be desirable to extend the time period for treatment significantly, however, where one or more days (e.g. 1, 2, 3, 4, 5, 6, 7 or 8 days) or one or more weeks (e.g. 1, 2, 3, 4, 5, 6, 7 or 8 days) lapse between the respective administrations. In embodiments where the ancillary agent is administered separately to the CD14 antagonist antibody, it will be understood that the ancillary agent can be administered by a method which is different to that of the administration method used for the CD14 antagonist antibody.

Where two or more therapeutic agents are administered to a subject "in conjunction" or "concurrently" they may be administered in a single composition at the same time, or in separate compositions at the same time, or in separate compositions separated in time.

2.3 Compositions

As described herein, the use of a CD14 antagonist antibody, whether alone or in combination with ancillary agents, can treat acute neuroinflammatory injury, such as, but not limited to, stroke (e.g. ischemic stroke or hemorrhagic stroke), hypoxic-ischemic brain injury, traumatic brain injury, subarachnoid hemorrhage and intracerebral hemorrhage. The CD14 antagonist antibody and optionally the ancillary agent can be administered either by themselves or with a pharmaceutically acceptable carrier. Thus, also provided herein are compositions a CD14 antagonist antibody for use in treating an acute neuroinflammatory injury.

The CD14 antagonist antibodies may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient (e.g. patient) thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for systemic administration, including intravenous, intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid. The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly (lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

A CD14 antagonist antibody and optionally an ancillary agent may also be administered directly to the airways in the form of an aerosol. For use as aerosols, the inhibitors of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

One of skill in the art will recognize that formulations are routinely designed according to their intended use, i.e. route of administration.

3. Methods of Treatment

The present disclosure provides for therapeutic methods of treating a subject with an acute neuroinflammatory injury. These methods therefore include within their scope the treatment of stroke (e.g. ischemic stroke or hemorrhagic stroke), hypoxic-ischemic brain injury, traumatic brain injury, subarachnoid hemorrhage and intracerebral hemorrhage in a subject, such as a human subject.

Contemplated herein are therefore methods for treating an acute neuroinflammatory injury in a subject by administering to the subject a CD14 antagonist antibody, and optionally an ancillary agent. The CD14 antagonist antibody, and optionally the ancillary agent (collectively referred to herein as "therapeutic agents"), will be administered in an "effective amount (s)", to achieve an intended purpose in a subject, such as the reduction or prevention of one or more symptoms of an acute neuroinflammatory injury. The dose of therapeutic agents(s) administered to a patient should be sufficient to achieve a beneficial response in the subject, such as a reduction in at least one symptom. In some embodiments of the present methods, the CD14 antagonist antibody is administered alone, i.e. no other active or therapeutic agent is administered to the subject over the course of treatment of the acute neuroinflammatory injury. In other examples, the only other active or therapeutic agent administered to the subject is a thrombolytic agent.

The quantity or dose frequency of the therapeutic agent(s) to be administered may depend on the subject to be treated inclusive of the age, sex, weight and general health condition thereof. In this regard, precise amounts of the therapeutic agent(s) for administration will depend on the judgment of the practitioner. One skilled in the art would be able, by routine experimentation, to determine an effective, non-toxic amount of a CD14 antagonist antibody, and optionally an ancillary agent described herein, for administration to a subject. In particular examples, the amount of CD14 antagonist antibody administered to a subject is between 0.1 mg/kg and 50 mg/kg, between 0.5 mg/kg and 40 mg/kg, between 2 mg/kg and 20 mg/kg or between 5 mg/kg and 10 mg/kg. In particular examples, the amount of CD14 antagonist antibody administered to a subject is (or is about) 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg/kg.

The CD14 antagonist antibody may be administered to the subject as a single dose or multiple doses. In particular embodiments, the CD14 antagonist antibody is administered as a single dose (e.g. a single bolus injection or a single discrete infusion). In embodiments where the CD14 antagonist antibody is administered as multiple doses, preferably no more than 3 doses are administered, and these are administered within about 6 hours, 12 hours, 18 hours, 24 hours, 36 hours, 48 hours, 60 hours or 72 hours of one another. In particular embodiments, only 1, 2, or 3 doses of the CD14 antagonist antibody is administered.

Typically, the CD14 antagonist antibody is administered to the subject in the acute phase of injury (e.g. 6-48 hours post-injury) or early subacute phase of injury (e.g. 48-96 hours post-injury). Thus, in exemplary embodiments, the CD14 antagonist antibody is administered to the subject at any time up to 4 days post-injury (e.g. 4 days post-stroke). In one example, the CD14 antagonist antibody is administered to the subject up to 6, 8, 10, 12, 18, 24, 36, 48, 60, 72, 84 or 96 hours post-injury (e.g. post-stroke). For example, the CD14 antagonist antibody may administered to the subject in a single dose up to 6, 8, 10, 12, 18, 24, 36, 48, 60, 72, 84 or 96 hours post-injury. In another example, the CD14 antagonist antibody is administered to the subject in two doses up to 6, 8, 10, 12, 18, 24, 36, 48, 60, 72, 84 or 96 hours post-injury. For example, the first dose may be administered up to 24 hours post-injury, and the second dose may be administered a further 24-48 hours later.

In particular examples, the CD14 antagonist antibody is administered to the subject between 2 and 96 hours, between 4 and 96 hours, between 6 and 96 hours, between 2 and 72 hours, between 4 and 72 hours, between 6 and 72 hours, between 2 and 48 hours, between 4 and 48 hours, between 6 and 48 hours, between 2 and 24 hours, between 4 and 24 hours, between 6 and 24 hours, between 2 and 18 hours, between 4 and 18 hours, between 6 and 18 hours, between 2 and 12 hours, between 4 and 12 hours, or between 6 and 12 hours post-injury.

In order that the invention may be readily understood and put into practical effect, particular preferred embodiments will now be described by way of the following non-limiting example.

EXAMPLES

Example 1

Material and Methods

CD14 Antagonist Antibody

The active agent used in the studies was a $F(Ab')_2$ fragment of mouse anti-mouse CD14 mAb (biG53) that is commercially available. The biG53 $F(Ab')_2$ antibody was chosen as the best surrogate for the anti-human CD14 mAb (IC14) currently used in human and in vitro studies. IC14 blocks PAMP and DAMP-dependent cytokine production in healthy human subjects and in human microglia/monocytes in vitro (FIG. 1). The species specificity of IC14 is restricted to human, nonhuman primate, and porcine CD14, limiting its utility in rodents. Therefore, a surrogate antibody the $F(Ab')_2$ fragment of the biG53 anti-mouse CD14 was manufactured. This reagent has a low endotoxin/azide-free formulation, is not immunogenic in mice, and lacks the Fc domain that mediates antibody and complement dependent cytotoxicity reflecting properties of Implicit Biosciences IC14. It was demonstrated that this anti-CD14 $F(Ab')_2$ functionally inhibits PAMP-dependent cytokine production in a dose dependent manner similar to that observed with IC14 in human microglia/monocytes (FIG. 1C).

Induction of Stroke in Mice by Filament Occlusion

The intraluminal middle cerebral artery occlusion (MCAO) animal model is accepted as one of the best for studying the most common form of stroke in humans, that is, stroke due to a blockage in the middle cerebral artery. In this model, under anesthetic, a fine gauge suture was threaded up through the external carotid artery of a mouse until it reached the middle cerebral artery, blocking blood flow to one side of the brain assessed using laser doppler. Groups of mice had the thread removed after 30 minutes and blood flow was restored. This resulted in damage to the ipsilateral striatum of the mice and changes in behavior upon waking, including circling to the left.

Treatment Regimen

Mice were administered either a) a single intravenous dose of 5 mg/kg of the biG53 $F(Ab')_2$ antibody via tail vein injection on day 1 at 6-hours post stroke, orb) a single intravenous dose of 5 mg/kg of the biG53 $F(Ab')_2$ antibody via tail vein injection on day 1 at 6-hours post stroke and subsequent daily intraperitoneal 5 mg/kg doses of the biG53 $F(Ab')_2$ antibody for 7 days. Control groups that were administered vehicle-only were also included in the study.

Functional Assessment

All behavioural tests were conducted blind to treatment. Testing was conducted prior to and after stroke at 24, 48, 72 hours and 7 days. The following behavioural tests were used in this interim analysis.

Mice were scored on two 28 point scales, according to the method of Clark et al. (Neurol. Res. 1997, 19:641-8). The General Score, which examined the general well-being of the animal, including any changes to the hair, ears, eyes, or posture, the level of spontaneous activity, and any epileptic-type behaviour; and the Focal Score, which examined stroke-specific deficits including body symmetry, gait, climbing ability, circling behaviour, front limb symmetry, and whisker response (McCann et al. PLoS One 9, 2014, e110602). Forepaw weight support was evaluated using the rota-rod test, and forepaw dexterity was determined by the Hang-wire test (Balkaya et al. Behay. Brain Res. 2018, 352:161-171).

Brain Processing

At the end of the study period (7 days post-stroke) mice were humanely euthanised by cervical dislocation and fore-brains collected for histological processing. Serial 16 μm coronal sections were prepared at 6 pre-determined levels (−3.2 to 6.8 mm relative to skull bregma) to encompass the frontal and parietal cortex and dorsal and ventral striatum.

Infarct Size and Monocyte/Macrophage and Microglia Activation

Dual NeuN/IBa-1 immunofluorescent staining of processed sections was used to assess infarct size and innate immune cell activation using previously defined methodology (McCann et al. PLoS One 9, 2014, e110602; Abeysinghe et al. Stem Cell Res. Ther. 2018, 6:186). Triplicate sections from each level were visualized with an Olympus (Albertslund, Denmark) microscope and stroke-damaged regions were identified as areas with distinct absence of NeuN stain, which was analyzed using ImageJ software (NIH, Bethesda, MD, USA).

Example 2

Effect of Treatment with CD14 Antagonist Antibody in Mice with MCAO

Mice with MCAO subsequently treated with the CD14 antagonist antibody or vehicle only, were assessed to determine functional decline and neurological deficit, as well as infarct size.

Functional Decline and Neurological Deficit

Figure 2:
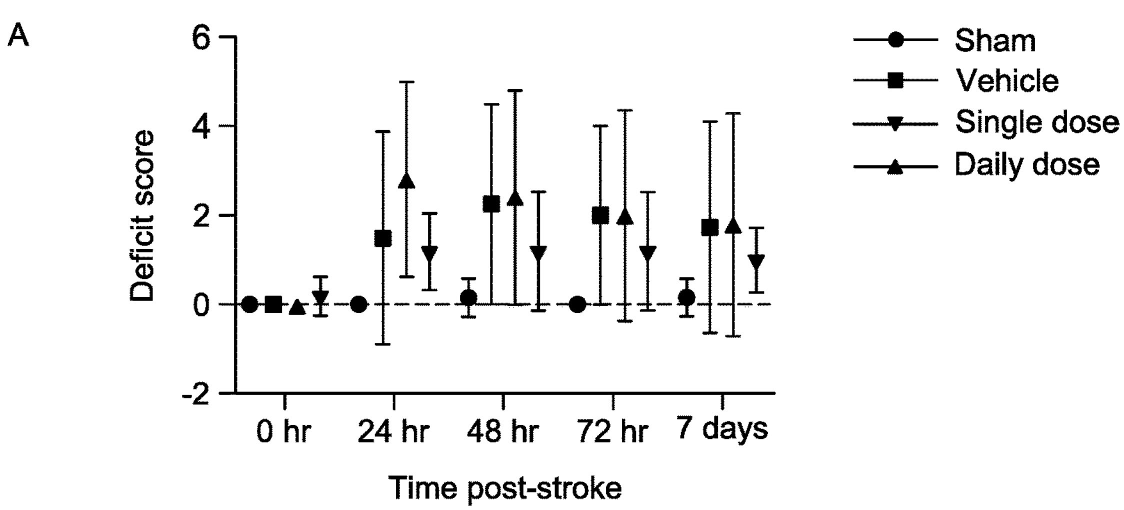
FIG. 2 is a graphical representation showing the effect of treatment with anti-CD14 as a single dose 6-hours post stroke, or daily doses over 7 days, on the functional decline in mice. Effects of anti-CD14 F(Ab')2 treatment on (A) body torsion, forelimb flexion, coat condition, weight loss and vocalization; ability to remain suspended from a wire; and ability to remain on an accelerating Rota-rod, each assessed 24-hrs to 7-days after a 30 min middle cerebral artery occlusion (MCAO). (A) Neuroscore results for assessment of body torsion, forelimb flexion, coat condition, weight loss and vocalization. (B) Hangwire test results. (C) Rota Rod Results. Data presented as mean±S.E.M (n=5/ group).
Figure 2:
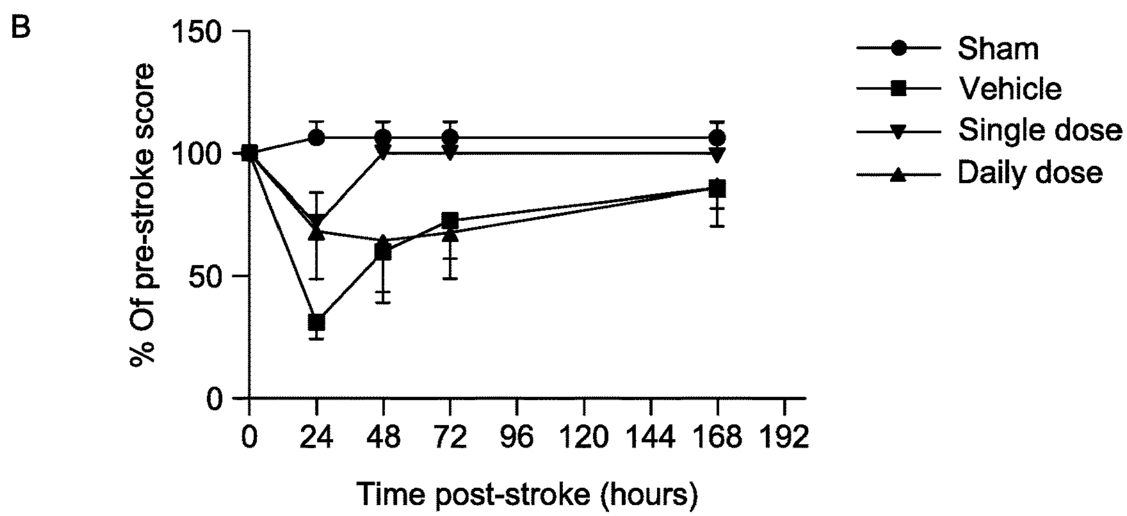
Figure 2:
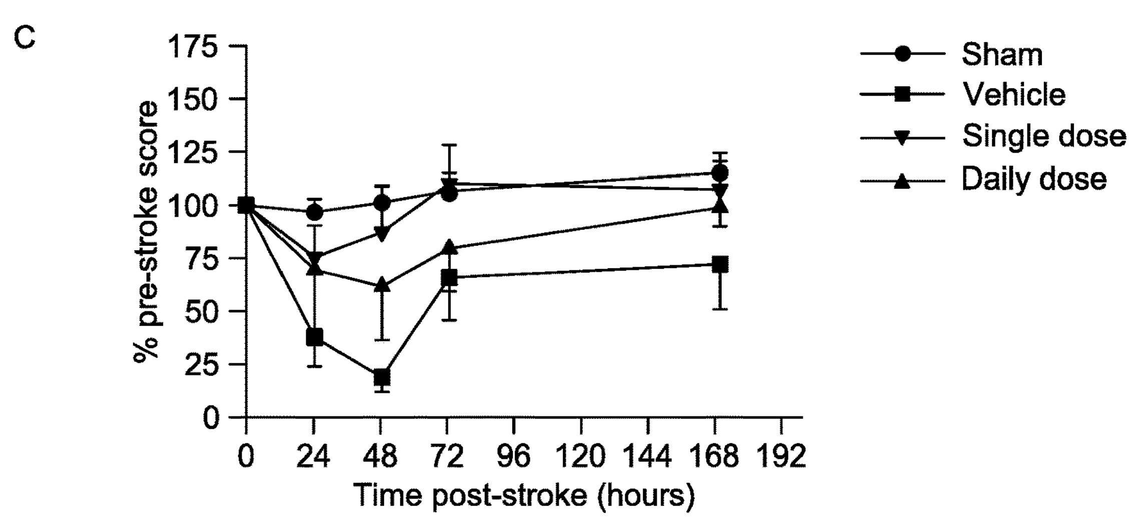

As shown in FIG. 2, stroke induced significant functional decline in vehicle treated control mice over 7-days, with peak decline detected at 24 hours using the hang wire test, and at 48 hours using neuroscore and Rota Rod assessments. Notably, functional decline at 24 hours was attenuated in the group of mice administered a single dose of anti-CD14 F(Ab') at 6 hours post-stroke, with performance in all tests returning to pre-stroke baseline scores and that of surgical sham control animals by 72 hours. Interestingly however, this attenuation of functional decline was not observed in the group of mice given a daily dose of anti-CD14 F(Ab')2 over 7 days.

Infarct Size

Figure 3:
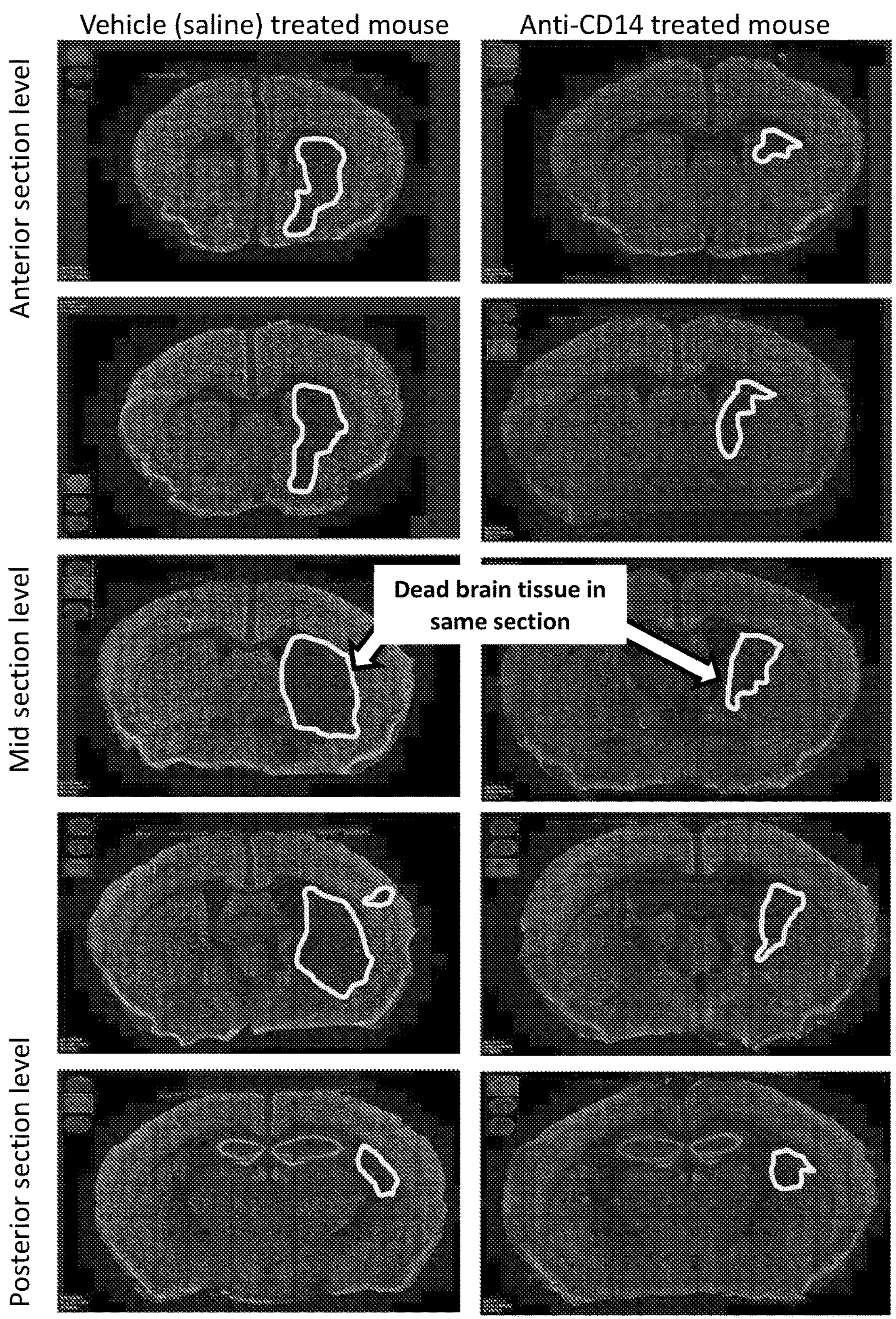
FIG. 3 shows NeuN staining of (A) vehicle (PBS) control, and (B) anti-CD14 treated mice of 5 horizontal sections anterior to posterior of the brain following MCAO.
Figure 4:
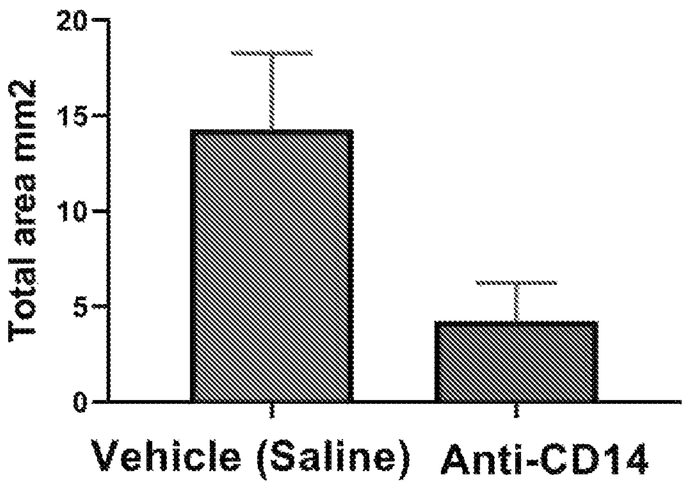
FIG. 4 is a graphical representation of the quantification of infarct size in anti-CD14 treated mice and vehicle (PBS) controls 7 days post-MCAO.
Figure 5:
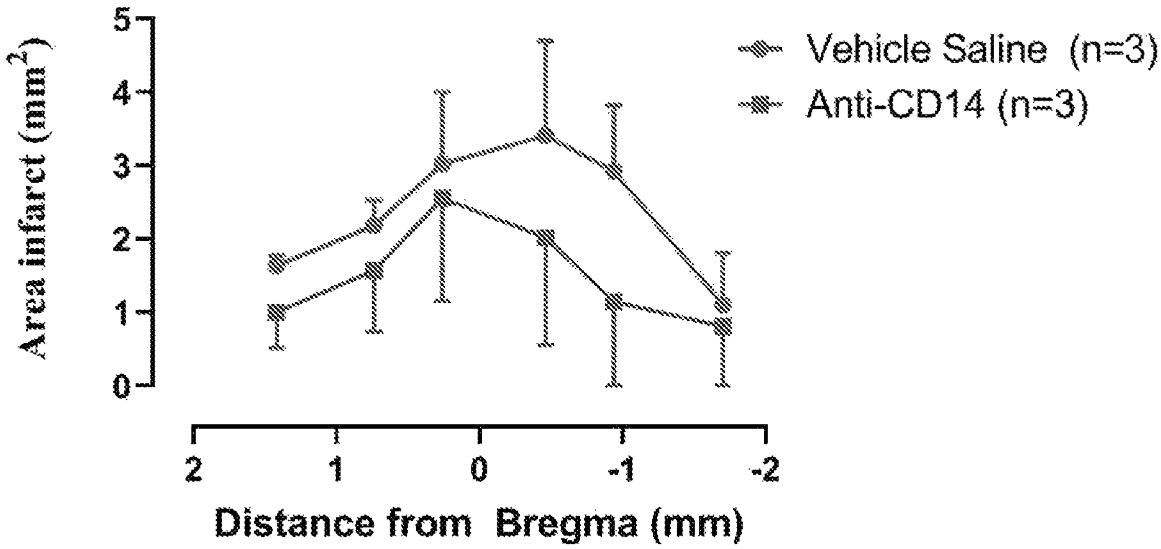
FIG. 5 is a graphical representation of the distribution area of damage in anti-CD14 treated mice and vehicle (PBS) controls 7 days post-MCAO.

NeuN immunofluorescent staining whole brain section anterior to posterior showed a deceased infarct size for treated animals versus non-treated animals (FIG. 3). Quantification of the total damage area across all sections (n=3 mice for both vehicle and anti-CD14 treated animals) confirmed the histological observations with treated animals exhibiting a 3-4-fold decrease in overall damage (FIG. 4). In addition, the damage reduction in treated mice was mostly observed in areas of the brain that showed the most damage in the untreated mice (FIG. 5).

Discussion

The data demonstrate that targeting CD14 in the acute phase of stroke improves outcomes both functionally and histologically. Conversely, extended treatment over 7 days was less effective. Functional and neurological decline are human relevant measures of successful therapeutic outcomes in stroke. The reduction of both these parameters in mice administered a single dose at 6 hours post-stroke indicates the potential for anti-CD14 therapy as a stroke interventional therapy for the acute and subacute treatment phase. Functional and neurological deficits are more relevant measures than reduction of infarct size as sometimes small infarcts can result in large functional and neurological decline in stroke patients. However, the reduction in infarct size in the treated mice is also encouraging, as it is now known that evidence of neuronal survival along the cortico-motor spinal tract after stroke is a positive predictor of functional recovery (Stinear, Lancet Neurol. 2017, 16:826-836).

The reduction of infarct size and total area of the brain damaged in treated mice indicates that the anti-CD14 therapy reduces expansion of the ischemic core into the penumbra (area of risk) during the acute phase of stroke in mice and has potential therapeutic benefits. Given the mode of action of an anti-CD14 therapy in attenuating DAMP signaling, these data suggest that a short, acute dose of an anti-CD14 antibody is able to attenuate the proinflammatory innate immune response that drives detrimental outcomes in first days following a stroke and that this results in clinically relevant beneficial outcomes.

Most stroke patients will not be diagnosed until 6-12 hours post-event. Therefore, any stroke intervention needs to be efficacious at a minimum of 6-hours post-stroke. Current thrombolytic treatments are only able to be used within 3-hours post stroke because use beyond this time may result in a dangerous hemorrhage in the brain. Therefore anti-CD14 intervention at 6-hours post stroke demonstrated in this study represents a clinical improvement on current thrombolytics that only target the removal of the clot and do not modify the detrimental local and global effects of the innate immune system in response to the stroke.

The disclosure of every patent, patent application, and publication cited herein is hereby incorporated herein by reference in its entirety.

The citation of any reference herein should not be construed as an admission that such reference is available as “Prior Art” to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

SEQUENCE LISTING

<160> NUMBER OF SEQ ID NOS: 26

<210> SEQ ID NO 1
<211> LENGTH: 106
<212> TYPE: PRT
<213> ORGANISM: Mus musculus

<400> SEQUENCE: 1

```
Gln Ser Pro Ala Ser Leu Ala Val Ser Leu Gly Gln Arg Ala Thr Ile
1               5                   10                  15

Ser Cys Arg Ala Ser Glu Ser Val Asp Ser Phe Gly Asn Ser Phe Met
            20                  25                  30

His Trp Tyr Gln Gln Lys Ala Gly Gln Pro Pro Lys Ser Ser Ile Tyr
        35                  40                  45

Arg Ala Ala Asn Leu Glu Ser Gly Ile Pro Ala Arg Phe Ser Gly Ser
    50                  55                  60

Gly Ser Arg Thr Asp Phe Thr Leu Thr Ile Asn Pro Val Glu Ala Asp
65                  70                  75                  80

Asp Val Ala Thr Tyr Phe Cys Gln Gln Ser Tyr Glu Asp Pro Trp Thr
                85                  90                  95

Phe Gly Gly Gly Thr Lys Leu Gly Asn Gln
            100                 105
```

<210> SEQ ID NO 2
<211> LENGTH: 105
<212> TYPE: PRT
<213> ORGANISM: Mus musculus

<400> SEQUENCE: 2

```
Leu Val Lys Pro Gly Gly Ser Leu Lys Leu Ser Cys Val Ala Ser Gly
1               5                   10                  15

Phe Thr Phe Ser Ser Tyr Ala Met Ser Trp Val Arg Gln Thr Pro Glu
            20                  25                  30

Lys Arg Leu Glu Trp Val Ala Ser Ile Ser Ser Gly Gly Thr Thr Tyr
        35                  40                  45

Tyr Pro Asp Asn Val Lys Gly Arg Phe Thr Ile Ser Arg Asp Asn Ala
    50                  55                  60

Arg Asn Ile Leu Tyr Leu Gln Met Ser Ser Leu Arg Ser Glu Asp Thr
65                  70                  75                  80

Ala Met Tyr Tyr Cys Ala Arg Gly Tyr Tyr Asp Tyr His Tyr Trp Gly
                85                  90                  95

Gln Gly Thr Thr Leu Thr Val Ser Ser
            100                 105
```

<210> SEQ ID NO 3
<211> LENGTH: 106
<212> TYPE: PRT
<213> ORGANISM: Mus musculus

<400> SEQUENCE: 3

```
Gln Ser Pro Ala Ser Leu Ala Val Ser Leu Gly Gln Arg Ala Thr Ile
1               5                   10                  15

Ser Cys Arg Ala Ser Glu Ser Val Asp Ser Tyr Val Asn Ser Phe Leu
            20                  25                  30

His Trp Tyr Gln Gln Lys Pro Gly Gln Pro Pro Lys Leu Leu Ile Tyr
        35                  40                  45

Arg Ala Ser Asn Leu Gln Ser Gly Ile Pro Ala Arg Phe Ser Gly Ser
    50                  55                  60
```

```
Gly Ser Arg Thr Asp Phe Thr Leu Thr Ile Asn Pro Val Glu Ala Asp
65                  70                  75                  80

Asp Val Ala Thr Tyr Cys Cys Gln Gln Ser Asn Glu Asp Pro Thr Thr
                85                  90                  95

Phe Gly Gly Gly Thr Lys Leu Glu Ile Lys
            100                 105


<210> SEQ ID NO 4
<211> LENGTH: 112
<212> TYPE: PRT
<213> ORGANISM: Mus musculus

<400> SEQUENCE: 4

Leu Gln Gln Ser Gly Pro Gly Leu Val Lys Pro Ser Gln Ser Leu Ser
1               5                   10                  15

Leu Thr Cys Thr Val Thr Gly Tyr Ser Ile Thr Ser Asp Ser Ala Trp
            20                  25                  30

Asn Trp Ile Arg Gln Phe Pro Gly Asn Arg Leu Glu Trp Met Gly Tyr
        35                  40                  45

Ile Ser Tyr Ser Gly Ser Thr Ser Tyr Asn Pro Ser Leu Lys Ser Arg
    50                  55                  60

Ile Ser Ile Thr Arg Asp Thr Ser Lys Asn Gln Phe Phe Leu Gln Leu
65                  70                  75                  80

Asn Ser Val Thr Thr Glu Asp Thr Ala Thr Tyr Tyr Cys Val Arg Gly
                85                  90                  95

Leu Arg Phe Ala Tyr Trp Gly Gln Gly Thr Leu Val Thr Val Ser Ala
            100                 105                 110


<210> SEQ ID NO 5
<211> LENGTH: 101
<212> TYPE: PRT
<213> ORGANISM: Mus musculus

<400> SEQUENCE: 5

Gln Thr Pro Ser Ser Leu Ser Ala Ser Leu Gly Asp Arg Val Thr Ile
1               5                   10                  15

Ser Cys Arg Ala Ser Gln Asp Ile Lys Asn Tyr Leu Asn Trp Tyr Gln
            20                  25                  30

Gln Pro Gly Gly Thr Val Lys Val Leu Ile Tyr Tyr Thr Ser Arg Leu
        35                  40                  45

His Ser Gly Val Pro Ser Arg Phe Ser Gly Ser Gly Ser Gly Thr Asp
    50                  55                  60

Tyr Ser Leu Thr Ile Ser Asn Leu Glu Gln Glu Asp Phe Ala Thr Tyr
65                  70                  75                  80

Phe Cys Gln Arg Gly Asp Thr Leu Pro Trp Thr Phe Gly Gly Gly Thr
                85                  90                  95

Lys Leu Glu Ile Lys
            100


<210> SEQ ID NO 6
<211> LENGTH: 116
<212> TYPE: PRT
<213> ORGANISM: Mus musculus

<400> SEQUENCE: 6

Leu Glu Ser Gly Pro Gly Leu Val Ala Pro Ser Gln Ser Leu Ser Ile
1               5                   10                  15
```

```
Thr Cys Thr Val Ser Gly Phe Ser Leu Thr Asn Tyr Asp Ile Ser Trp
            20                  25                  30

Ile Arg Gln Pro Pro Gly Lys Gly Leu Glu Trp Leu Gly Val Ile Trp
        35                  40                  45

Thr Ser Gly Gly Thr Asn Tyr Asn Ser Ala Phe Met Ser Arg Leu Ser
    50                  55                  60

Ile Thr Lys Asp Asn Ser Glu Ser Gln Val Phe Leu Lys Met Asn Gly
65                  70                  75                  80

Leu Gln Thr Asp Asp Thr Gly Ile Tyr Tyr Cys Val Arg Gly Asp Gly
                85                  90                  95

Asn Phe Tyr Leu Tyr Asn Phe Asp Tyr Trp Gly Gln Gly Thr Thr Leu
            100                 105                 110

Thr Val Ser Ser
        115


<210> SEQ ID NO 7
<211> LENGTH: 15
<212> TYPE: PRT
<213> ORGANISM: Mus musculus

<400> SEQUENCE: 7

Arg Ala Ser Glu Ser Val Asp Ser Phe Gly Asn Ser Phe Met His
1               5                   10                  15


<210> SEQ ID NO 8
<211> LENGTH: 7
<212> TYPE: PRT
<213> ORGANISM: Mus musculus

<400> SEQUENCE: 8

Arg Ala Ala Asn Leu Glu Ser
1               5


<210> SEQ ID NO 9
<211> LENGTH: 9
<212> TYPE: PRT
<213> ORGANISM: Mus musculus

<400> SEQUENCE: 9

Gln Gln Ser Tyr Glu Asp Pro Trp Thr
1               5


<210> SEQ ID NO 10
<211> LENGTH: 5
<212> TYPE: PRT
<213> ORGANISM: Mus musculus

<400> SEQUENCE: 10

Ser Tyr Ala Met Ser
1               5


<210> SEQ ID NO 11
<211> LENGTH: 16
<212> TYPE: PRT
<213> ORGANISM: Mus musculus

<400> SEQUENCE: 11

Ser Ile Ser Ser Gly Gly Thr Thr Tyr Tyr Pro Asp Asn Val Lys Gly
1               5                   10                  15


<210> SEQ ID NO 12
<211> LENGTH: 7
```

<212> TYPE: PRT
<213> ORGANISM: Mus musculus

<400> SEQUENCE: 12

Gly Tyr Tyr Asp Tyr His Tyr
1 5

<210> SEQ ID NO 13
<211> LENGTH: 15
<212> TYPE: PRT
<213> ORGANISM: Mus musculus

<400> SEQUENCE: 13

Arg Ala Ser Glu Ser Val Asp Ser Tyr Val Asn Ser Phe Leu His
1 5 10 15

<210> SEQ ID NO 14
<211> LENGTH: 7
<212> TYPE: PRT
<213> ORGANISM: Mus musculus

<400> SEQUENCE: 14

Arg Ala Ser Asn Leu Gln Ser
1 5

<210> SEQ ID NO 15
<211> LENGTH: 9
<212> TYPE: PRT
<213> ORGANISM: Mus musculus

<400> SEQUENCE: 15

Gln Gln Ser Asn Glu Asp Pro Thr Thr
1 5

<210> SEQ ID NO 16
<211> LENGTH: 6
<212> TYPE: PRT
<213> ORGANISM: Mus musculus

<400> SEQUENCE: 16

Ser Asp Ser Ala Trp Asn
1 5

<210> SEQ ID NO 17
<211> LENGTH: 16
<212> TYPE: PRT
<213> ORGANISM: Mus musculus

<400> SEQUENCE: 17

Tyr Ile Ser Tyr Ser Gly Ser Thr Ser Tyr Asn Pro Ser Leu Lys Ser
1 5 10 15

<210> SEQ ID NO 18
<211> LENGTH: 6
<212> TYPE: PRT
<213> ORGANISM: Mus musculus

<400> SEQUENCE: 18

Gly Leu Arg Phe Ala Tyr
1 5

<210> SEQ ID NO 19
<211> LENGTH: 11
<212> TYPE: PRT
<213> ORGANISM: Mus musculus

<400> SEQUENCE: 19

Arg Ala Ser Gln Asp Ile Lys Asn Tyr Leu Asn
1 5 10

<210> SEQ ID NO 20
<211> LENGTH: 7
<212> TYPE: PRT
<213> ORGANISM: Mus musculus

<400> SEQUENCE: 20

Tyr Thr Ser Arg Leu His Ser
1 5

<210> SEQ ID NO 21
<211> LENGTH: 9
<212> TYPE: PRT
<213> ORGANISM: Mus musculus

<400> SEQUENCE: 21

Gln Arg Gly Asp Thr Leu Pro Trp Thr
1 5

<210> SEQ ID NO 22
<211> LENGTH: 5
<212> TYPE: PRT
<213> ORGANISM: Mus musculus

<400> SEQUENCE: 22

Asn Tyr Asp Ile Ser
1 5

<210> SEQ ID NO 23
<211> LENGTH: 16
<212> TYPE: PRT
<213> ORGANISM: Mus musculus

<400> SEQUENCE: 23

Val Ile Trp Thr Ser Gly Gly Thr Asn Tyr Asn Ser Ala Phe Met Ser
1 5 10 15

<210> SEQ ID NO 24
<211> LENGTH: 12
<212> TYPE: PRT
<213> ORGANISM: Mus musculus

<400> SEQUENCE: 24

Gly Asp Gly Asn Phe Tyr Leu Tyr Asn Phe Asp Tyr
1 5 10

<210> SEQ ID NO 25
<211> LENGTH: 238
<212> TYPE: PRT
<213> ORGANISM: Artificial Sequence
<220> FEATURE:
<223> OTHER INFORMATION: IC14 variable light chain domain

<400> SEQUENCE: 25

Met Glu Thr Asp Thr Ile Leu Leu Trp Val Leu Leu Leu Trp Val Pro
1 5 10 15

Gly Ser Thr Gly Asp Ile Val Leu Thr Gln Ser Pro Ala Ser Leu Ala
20 25 30

Val Ser Leu Gly Gln Arg Ala Thr Ile Ser Cys Arg Ala Ser Glu Ser
35 40 45

```
Val Asp Ser Tyr Val Asn Ser Phe Leu His Trp Tyr Gln Gln Lys Pro
    50                  55                  60

Gly Gln Pro Pro Lys Leu Leu Ile Tyr Arg Ala Ser Asn Leu Gln Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235


<210> SEQ ID NO 26
<211> LENGTH: 460
<212> TYPE: PRT
<213> ORGANISM: Artificial Sequence
<220> FEATURE:
<223> OTHER INFORMATION: IC14 variable heavy chain domain

<400> SEQUENCE: 26

Met Lys Val Leu Ser Leu Leu Tyr Leu Leu Thr Ala Ile Pro Gly Ile
1               5                   10                  15

Leu Ser Asp Val Gln Leu Gln Gln Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Ser Ala Trp Asn Trp Ile Arg Gln Phe Pro Gly Asn Arg Leu
    50                  55                  60

Glu Trp Met Gly Tyr Ile Ser Tyr Ser Gly Ser Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Val Arg Gly Leu Arg Phe Ala Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175
```

-continued

```
Gly Ala Leu Thr Ser Gly Val His Thr Phe Pro Ala Val Leu Gln Ser
        180                 185                 190

Ser Gly Leu Tyr Ser Leu Ser Ser Val Val Thr Val Pro Ser Ser Ser
    195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Ser Cys Pro Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
        260                 265                 270

Thr Cys Val Val Val Asp Val Ser Gln Glu Asp Pro Glu Val Gln Phe
    275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
        340                 345                 350

Lys Gly Gln Pro Arg Glu Pro Gln Val Tyr Thr Leu Pro Pro Ser Gln
    355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
        420                 425                 430

Gly Asn Val Phe Ser Cys Ser Val Met His Glu Ala Leu His Asn His
    435                 440                 445

Tyr Thr Gln Lys Ser Leu Ser Leu Ser Leu Gly Lys
    450                 455                 460
```

What is claimed is:

1. A method for treating stroke in a human subject, comprising, consisting or consisting essentially of administering an effective amount of a CD14 antagonist antibody to the subject, wherein the antibody is administered to the subject up to 48 hours post-injury.

2. A method for treating stroke in a human subject, comprising, consisting or consisting essentially of systemically administering an effective amount of a CD14 antagonist antibody to the subject, wherein the antibody is administered alone.

3. A method for treating stroke in a human subject, comprising, consisting or consisting essentially of administering an effective amount of a CD14 antagonist antibody to the subject, wherein the antibody is administered as a single dose.

4. A method of treating stroke in a human subject, comprising, consisting or consisting essentially of administering an effective amount of a CD14 antagonist antibody to the subject, wherein the CD14 antagonist antibody is selected from:

(i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);

(ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (iii) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

5. The method of claim 3, wherein the antibody is administered to the subject up to 48 hours post-injury.

6. The method of claim 3, wherein the antibody is administered to the subject up to 24 hours post-injury.

7. The method of claim 3, wherein the antibody is administered to the subject between 2 and 48 hours post-injury.

8. The method of claim 3, wherein the antibody is selected from:

(i) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);

(ii) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and (iii) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

9. The method of claim 3, wherein the antibody is selected from:

(i) an antibody comprising:

a VL domain that comprises, consists or consists essentially of the sequence: QSPASLAVSLGQRATISCRASESVDSFGNSFMHWYQQKAGQPPKSSIYRAANLESGIPAR FSGSGSRTD FTLTINPVEADDVATYFCQQSYEDPWTFGGGTKLGNQ [SEQ ID NO: 1] (3C10 VL); and a VH domain that comprises, consists or consists essentially of the sequence: LVKPGGSLKLSCVASGFTFSSYAMSWVRQTPEKRLEWVASISSGGTTYYPDNVKGRFTI SRDNARNILYL QMSSLRSEDTAMYYCARGYYDYHYWGQGTTLTVSS [SEQ ID NO: 2] (3C10 VH);

(ii) an antibody comprising:

a VL domain that comprises, consists or consists essentially of the sequence: QSPASLAVSLGQRATISCRASESVDSYVNSFLHWYQQKPGQPPKLLIYRASNLQSGIPARFSGSGSRTDFTLTINPVEADDVATYCCQQSNEDPTTFGGGTKLEIK [SEQ ID NO: 3] (28C5 VL); and a VH domain that comprises, consists or consists essentially of the sequence: LQQSGPGLVKPSQSLSLTCTVTGYSITSDSAWNWIRQFPGNRLEWMGYISYSGSTSYN PSLKSRISITRD TSKNQFFLQLNSVTTEDTATYYCVRGLRFAYWGQGTLVTVSA [SEQ ID NO: 4] (28C5 VH); and (iii) an antibody comprising:

a VL domain that comprises, consists or consists essentially of the sequence: QTPSSLSASLGDRVTISCRASQDIKNYLNWYQQPGGTVKVLIYYTSRLHSGVPSRESGSG SGTDYSLTIS NLEQEDFATYFCQRGDTLPWTFGGGTKLEIK [SEQ ID NO: 5] (18E12 VL); and a VH domain that comprises, consists or consists essentially of the sequence: LESGPGLVAPSQSLSITCTVSGFSLTNYDISWIRQPPGKGLEWLGVIWTSGGTNYNSAFM SRLSITKDNS

ESQVFLKMNGLQTDDTGIYYCVRGDGNFYLYNFDYWGQGTTLTVSS [SEQ ID NO: 6] (18E12 VH).

10. The method according to claim 3, wherein the antibody is humanized or chimeric.

11. The method of claim 3, wherein the antibody comprises a light chain and a heavy chain, wherein:

```
the light chain comprises the amino acid sequence:
                                   [SEQ ID NO: 25]
METDTILLWVLLLWVPGSTGDIVLTQSPASLAVSLGQRATISCRASESVD

SYVNSFLHWYQQKPGQPPKLLIYRASNLQSGIPARFSGSGSRTDFTLTIN

PVEADDVATYYCQQSNEDPYTFGGGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC;
and

the heavy chain comprises the amino acid sequence:
                                   [SEQ ID NO: 26]
MKVLSLLYLLTAIPGILSDVQLQQSGPGLVKPSQSLSLTCTVTGYSITSD

SAWNWIRQFPGNRLEWMGYISYSGSTSYNPSLKSRISITRDTSKNQFFLQ

LNSVTTEDTATYYCVRGLRFAYWGQGTLVTVSSASTKGPSVFPLAPCSRS

TSESTAALGCLVKDYFPEPVTVSWNSGALTSGVHTFPAVLQSSGLYSLSS
```

-continued

```
VVTVPSSSLGTKTYTCNVDHKPSNTKVDKRVESKYGPPCPSCPAPEFLGG

PSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHYT

QKSLSLSLGK.
```

12. The method of claim 3, wherein the antibody is the IC14 antibody.

13. The method of claim 3, wherein the stroke is ischemic stroke or hemorrhagic stroke.

14. The method of claim 3, wherein the antibody is administered systemically.

15. The method of claim 3, wherein the amount of antibody administered to the subject is between or is between about 0.1 mg/kg and 50 mg/kg.

16. The method of claim 3, wherein the amount of antibody administered to the subject is or is about 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg/kg.

* * * * *